(12) United States Patent
Trout, II et al.

(10) Patent No.: US 9,410,142 B2
(45) Date of Patent: Aug. 9, 2016

(54) DENDRIMER-BASED EXCIPIENTS FOR THE ATTENUATION OF PROTEIN AGGREGATION

(75) Inventors: Bernhardt L. Trout, II, Cambridge, MA (US); Diwakar Shukla, Stanford, CA (US); Curtiss P. Schneider, Melrose, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 357 days.

(21) Appl. No.: 13/884,420

(22) PCT Filed: Nov. 11, 2011

(86) PCT No.: PCT/US2011/060400
§ 371 (c)(1),
(2), (4) Date: Jun. 5, 2013

(87) PCT Pub. No.: WO2012/065082
PCT Pub. Date: May 18, 2012

(65) Prior Publication Data
US 2014/0004592 A1    Jan. 2, 2014

Related U.S. Application Data

(60) Provisional application No. 61/412,600, filed on Nov. 11, 2010.

(51) Int. Cl.
*C12N 9/96* (2006.01)
*C07C 279/12* (2006.01)

(52) U.S. Cl.
CPC ............... *C12N 9/96* (2013.01); *C07C 279/12* (2013.01)

(58) Field of Classification Search
CPC ................................ C07C 279/12; C12N 9/96
USPC .......................................... 564/153; 435/188
See application file for complete search history.

(56) References Cited

U.S. PATENT DOCUMENTS
2006/0127350 A1    6/2006 Heegaard et al.

FOREIGN PATENT DOCUMENTS
CA          2410224      * 12/2001
WO    WO 2012/047630   *  4/2012

OTHER PUBLICATIONS

Johnson, Biomacromolecules, vol. 11, No. 11, 2010, 3007-13.*
Beezer, A. E. et al., "Dedrimers as potential drug carriers; encapsulation of acidic hydrophobes within water soluble PAMAM derivatives", *Tetrahedron*, 59:3873-3880 (2003).
Radchatawedchakoon, W. et al., "Solid phase synthesis of novel asymmetric hydrophilic head cholesterol-based cationic lipids with potential DNA delivery", *Bioorganic and Medicinal Chemistry*, 18:330-342 (2010).
Shi, X. et al., "Capillary electrophoresis of polycationic poly(amidoamine) dendrimers", *Electrophoresis*, 26:2949-2959 (2005).
International Search Report and Written Opinion from parent application PCT/US2011/060400 dated Apr. 4, 2012.

* cited by examiner

*Primary Examiner* — Shailendra Kumar
(74) *Attorney, Agent, or Firm* — Dana M. Gordon; Foley Hoag LLP

(57) ABSTRACT

One aspect of the invention is a salt comprising guanidinium groups, as shown in formula I. Another aspect of the invention is a salt comprising guanidinium groups, as shown in formula II. Another aspect of the invention is a salt comprising guanidinium groups, as shown in formula III. Another aspect of the invention is a salt comprising guanidinium groups, as shown in formula IV. Yet another aspect of the invention is a salt comprising guanidinium groups, as shown in formula I, II, III, and IV further comprising independently for each occurrence citrate, phosphate, or sulfate anion. Also disclosed are compositions comprising a protein and a salt comprising guanidinium groups, as shown in formula I, II, III, and IV. Also provided are methods of increasing shelf life of an aqueous solution of a protein and decreasing the amount of protein aggregation in an aqueous solution of a protein.

19 Claims, 12 Drawing Sheets

DENDRIMER-BASED EXCIPIENTS FOR THE ATTENUATION OF PROTEIN AGGREGATION

RELATED APPLICATIONS

This application is the U.S. national phase of International Patent Application No. PCT/US2011/060,400, filed Nov. 11, 2011, which claims benefit under 35 U.S.C. §119(e) of U.S. Provisional Patent Application No. 61/412,600, filed on Nov. 11, 2010.

GOVERNMENT FUNDING

This invention was made with government support under Grant No. 5R21EB007043-2 awarded by the National Institutes of Health. The government has certain rights in this invention.

BACKGROUND OF THE INVENTION

Although protein-based therapeutics (e.g., monoclonal antibodies) are the fastest growing sector of the pharmaceutical industry, production costs remain incredibly high, and rapid commercialization of new protein drug candidates is not being widely realized. Both of these problems are due in part to the physical and chemical instabilities of proteins. Protein aggregation is arguably the most common and troubling manifestation of protein instability, occurring in almost all phases of development. Protein aggregates are usually normative in structure, may exhibit reduced biological activity, and can remain soluble or precipitate from solution. In addition to reducing the efficacy of a protein therapeutic, if administered to a patient aggregates can cause adverse reactions, such as immune response, sensitization, or even anaphylactic shock. To make the problem worse, for the practical application of traditional and novel drug delivery techniques protein-based therapeutics must be formulated at relatively high concentrations and preferentially remain stable for extended periods of time. The current approach toward stabilizing protein drugs against aggregation is trial-and-error testing of different combinations of cosolutes (e.g., salts, sugars, surfactants, amino acids) using empirically derived heuristics. While common, this approach is inefficient and does not always enable the discovery of stable protein solution formulations. Thus, many products must be lyophilized and reconstituted prior to injection, which is highly undesirable.

Due to the issues and complications associated with protein aggregation and the ineffectiveness of current stabilization methodologies, there is great interest in developing new solution additives that are effective at reducing or eliminating protein aggregation and are also effective at low concentrations.

SUMMARY OF THE INVENTION

One aspect of the invention is a salt comprising guanidinium groups, as shown in formula I. Another aspect of the invention is a salt comprising guanidinium groups, as shown in formula II. Another aspect of the invention is a salt comprising guanidinium groups, as shown in formula III. Another aspect of the invention is a salt comprising guanidinium groups, as shown in formula IV. Yet another aspect of the invention is a salt comprising guanidinium groups, as shown in formula I, II, III, and IV further comprising independently for each occurrence citrate, phosphate, or sulfate anion. Also disclosed are compositions comprised of a protein and a salt, further comprising guanidinium groups, as shown in formula I, II, III, and IV.

DETAILED DESCRIPTION OF THE INVENTION

Figure 1:
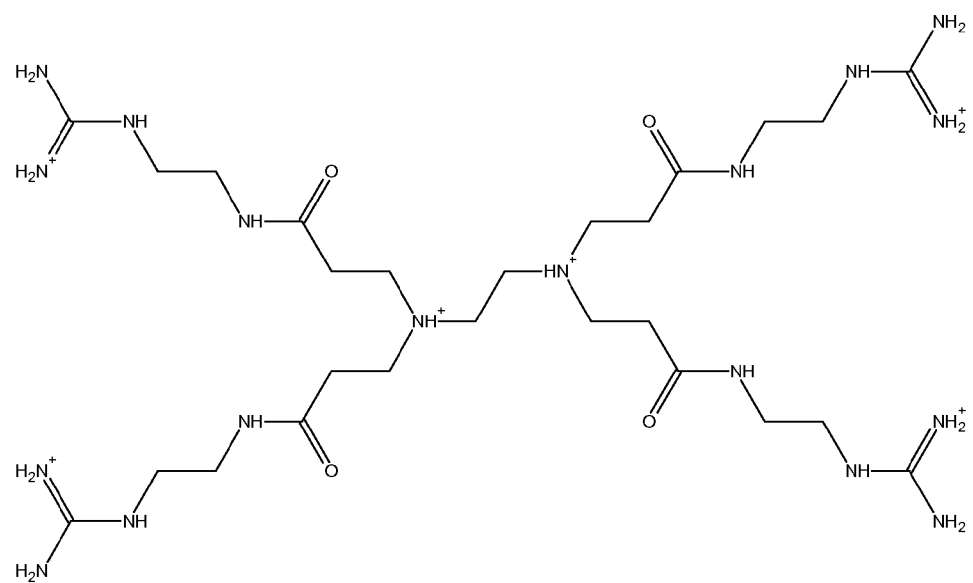
FIG. 1 shows the structure of a Generation 0 Polyamidoamine (PAMAM) dendrimer with a surface modified to guanidinium.

Remarkably, we have discovered and tested a new class of excipients that has the potential for widespread application as universal stabilizers of protein therapeutics, protein-based diagnostics, and other protein-based products used in research and clinical settings. When compared to commonly used excipients (e.g., sucrose, arginine hydrochloride, glycerol), the novel excipients of the present invention offer more than an order of magnitude improvement at suppressing the rate of aggregation of a model protein at elevated and room temperatures. As a result, if used in the formulation of a therapeutic, diagnostic, or other protein, the shelf life of the protein, at room or refrigerated temperatures, may be extended from a few weeks to several months or years. In addition, the novel excipients will be of use during typical laboratory techniques (e.g., dialysis, ultrafiltration, centrifugation, fermentation) in which protein stability is an issue, making them useful not only in diagnosis and treatment, but also in biotechnology research. Furthermore, the excipients will likely be useful during protein production and purification for improving yield and lowering downstream purification costs.

As mentioned, in addition to using these novel excipients for formulation, diagnostic, clinical, and research applications, a more immediate and potentially broader use will be as a stabilizer during development and production. Aggregation greatly reduces yield, places a huge burden on downstream purification steps, can cause filters and equipment to clog, and can delay the release of a new product. If properly used, the excipients of the invention can reduce aggregation during upstream processing. For example, they could be added to the fermentation liquid to reduce aggregation induced by elevated temperatures and agitation, added to the refolding buffer to reduce aggregation that occurs when inclusion bodies are dissolved in a denaturant and refolded, added to the solution prior to ultrafiltration to reduce the aggregation that occurs when the protein is concentrated, and added to the solution prior to dialysis to reduce the aggregation that occurs when the buffer is exchanged. In addition to these specific applications, the excipients can be used in other stages of production where aggregation is a nuisance (e.g., during steps where equipment often becomes clogged with aggregates, during intermittent storage in between steps). Moreover, experimental evidence suggests that the excipients will also improve recovery during initial separation processes (e.g., Protein A column elution under less harsh conditions). Furthermore, the excipients can easily be removed during normal polishing steps if they are not desired in the final solution. Therefore, another aspect of the invention is the use of excipients of the invention during typical production steps with the aim of reducing aggregation along with improving separation recovery.

Representative Compounds of the Invention

One aspect of the invention is a salt comprising guanidinium groups, as shown in formula I.

Another aspect of the invention is a salt comprising guanidinium groups, as shown in formula II.

Another aspect of the invention is a salt comprising guanidinium groups, as shown in formula III.

Another aspect of the invention is a salt comprising guanidinium groups, as shown in formula IV.

Yet another aspect of the invention is a salt comprising guanidinium groups, as shown in formula I, II, III, and IV, further comprising independently for each occurrence citrate, phosphate, or sulfate anion.

Also disclosed are compositions comprised of a protein and a salt, further comprising guanidinium groups, as shown in formula I, II, III, and IV.

One aspect of the invention relates to a salt, comprising a plurality of anions; and a cation represented by formula I:

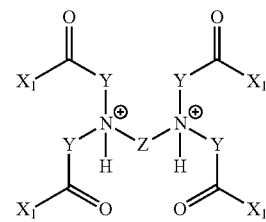

wherein, independently for each occurrence,
each anion is

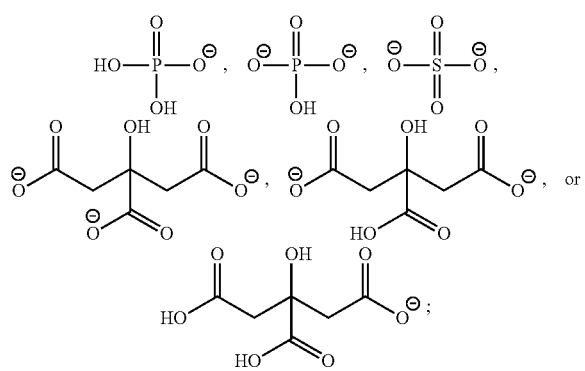

Z is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
Y is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
$X^1$ is

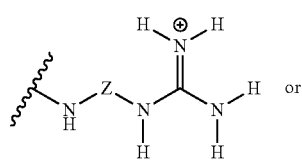 or

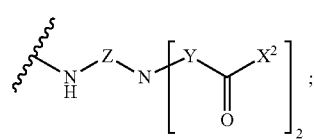

$X^2$ is

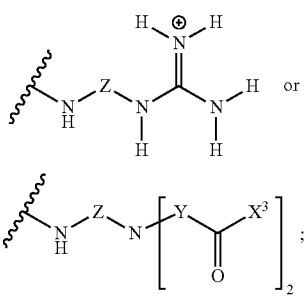

or

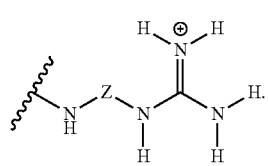

;

and
$X^3$ is

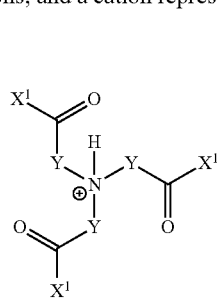

Another aspect of the invention relates to a salt, comprising a plurality of anions; and a cation represented by formula II:

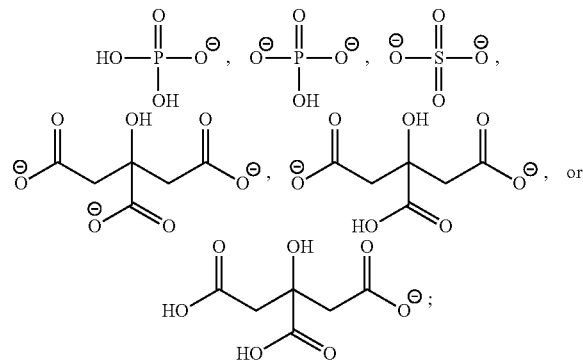

II wherein, independently for each occurrence,
each anion is phosphate, diphosphate, sulfate, citrate anions (as depicted); or Z is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
Y is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;

$X^1$ is

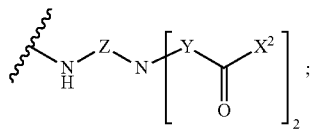

;

$X^2$ is

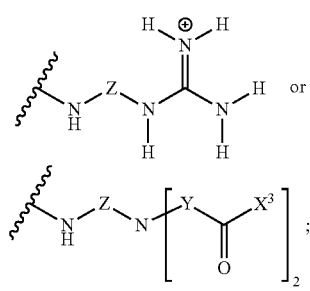

;

and
$X^3$ is

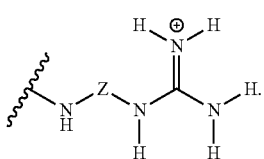

Another aspect of the invention relates to a salt, comprising a plurality of anions; and a cation represented by formula III:

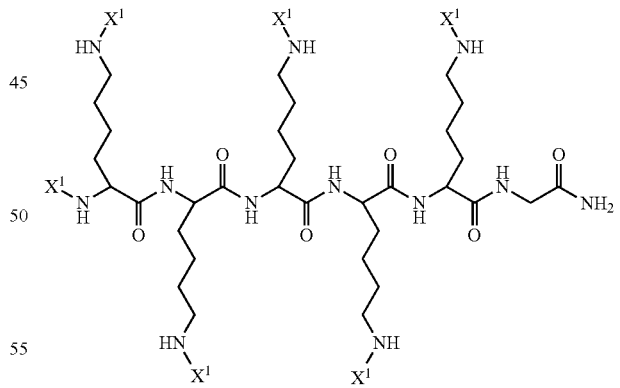

III wherein, independently for each occurrence,
each anion is

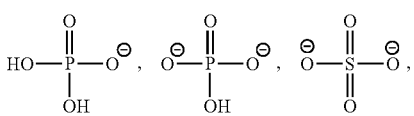

-continued
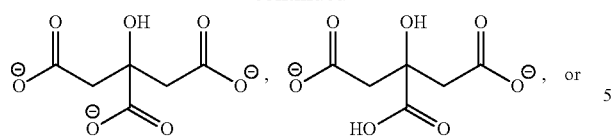
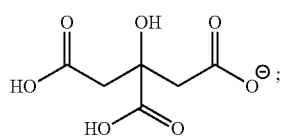
$X^1$ is
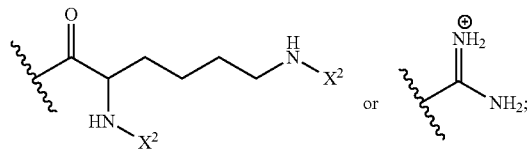
$X^2$ is
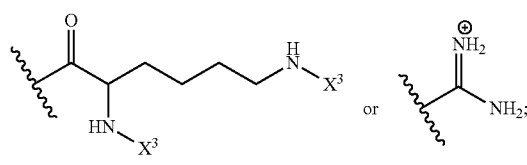
$X^3$ is
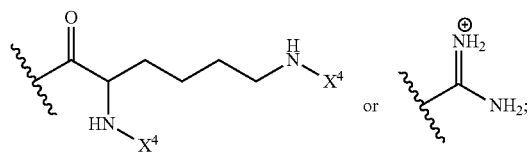
and
$X^4$ is
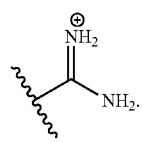 [SMILES: *C(N)=[NH2+]]
Another aspect of the invention relates to salt, comprising a plurality of anions; and a cation represented by formula IV:
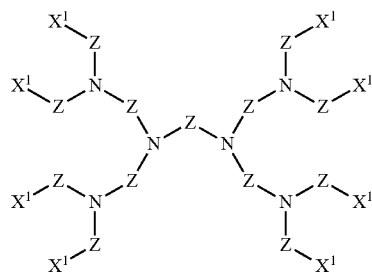
wherein, independently for each occurrence,
each anion is
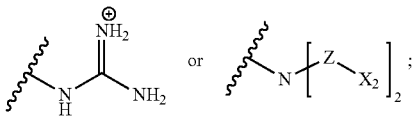
Z is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
$X^1$ is
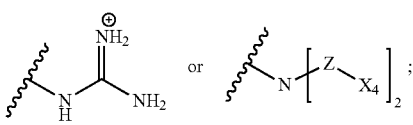
$X^2$ is
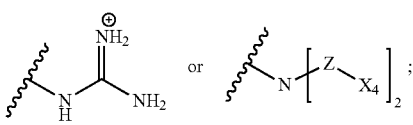
$X^3$ is
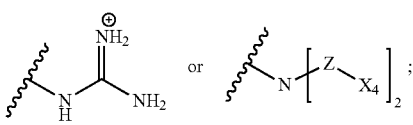

and
$X^4$ is

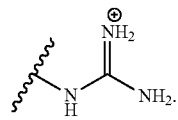

In certain embodiments, the invention relates to any one of the aforementioned salts, wherein $X^1$ is

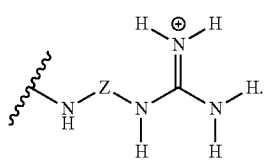

In certain embodiments, the invention relates to any one of the aforementioned salts, wherein $X^1$ is

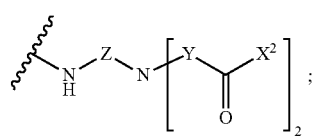

and $X^2$ is

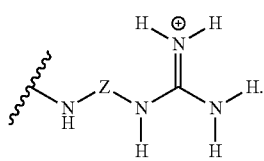

In certain embodiments, the invention relates to any one of the aforementioned salts, wherein $X^1$ is

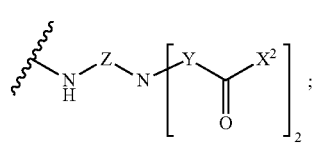

and $X^2$ is

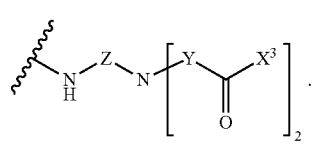

In certain embodiments, the invention relates to any one of the aforementioned salts, wherein Z is —CH$_2$CH$_2$—.

In certain embodiments, the invention relates to any one of the aforementioned salts, wherein Y is —CH$_2$CH$_2$—.

In certain embodiments, the invention relates to any one of the aforementioned salts, wherein Y is —CH$_2$CH$_2$—; and Z is —CH$_2$CH$_2$—.

In certain embodiments, the invention relates to any one of the aforementioned salts, wherein each anion is

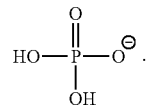

In certain embodiments, the invention relates to any one of the aforementioned salts, wherein each anion is

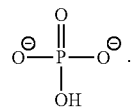

In certain embodiments, the invention relates to any one of the aforementioned salts, wherein each anion is

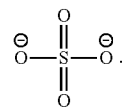

In certain embodiments, the invention relates to any one of the aforementioned salts, wherein each anion is

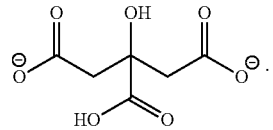 [SMILES: O=C([O-])CC(O)(CC(=O)[O-])C(=O)O]

In certain embodiments, the invention relates to any one of the aforementioned salts, wherein each anion is

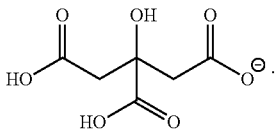 [SMILES: O=C([O-])CC(O)(CC(=O)O)C(=O)O]

Another aspect of the invention relates to a composition, comprising a protein; and any one of the aforementioned salts.

In certain embodiments, the aforementioned composition further comprises water.

Another aspect of the invention relates to a method of increasing the shelf life of an aqueous solution of a protein, comprising the step of combining an aqueous solution of a protein and an effective amount of any one of the salts of the present invention. The shelf life of an aqueous solution of a protein is deemed to be increased when the shelf life is at least one day longer than the shelf life of a suitable control aqueous solution of the protein without an effective amount of any one of the salts of the present invention. In one embodiment, the shelf life is increased by at least one day to at least one year.

In one embodiment, the shelf life is increased by one day to one year. In one embodiment, the shelf life is increased by more than one year. Generally shelf life relates to the time period during which at least a certain amount or percentage of a protein in a given formulation is present in a biologically active form. For example, the shelf life of an antibody may be the time period during which at least 90 percent of the antibody present in a given formulation has biological activity. Biological activity for a given protein can be measured using any suitable method, including suitable in vitro and/or in vivo methods. Selection of a method suitable for measuring activity of a particular protein is within the skill of persons familiar with such protein.

Another aspect of the invention relates to a method of decreasing the amount of protein aggregation in an aqueous solution of a protein, comprising the step of combining an aqueous solution of a protein and an effective amount of any one of the salts of the present invention. The amount of protein aggregation in an aqueous solution of a protein is deemed to be decreased when the amount of protein aggregation is less than or equal to 95 percent of the amount of protein aggregation of a suitable control aqueous solution of the protein without an effective amount of any one of the salts of the present invention. In various embodiments the decreased amount of protein aggregation is less than or equal to 1, 5, 10, 15, 20, 25, 30, 35, 40, 45, 50, 55, 60, 65, 70, 75, 80, 85, 90, or 95 percent of the amount of protein aggregation of a suitable control aqueous solution of the protein without an effective amount of any one of the salts of the present invention. For example, if a control aqueous solution of a protein without an effective amount of any one of the salts of the present invention has 10 percent aggregation, an aqueous solution of the protein with an effective amount of any one of the salts of the present invention may have only 1 percent aggregation, i.e., only 10 percent of the amount of protein aggregation of the control aqueous solution of the protein without an effective amount of any one of the salts of the present invention. Protein aggregation for a given protein can be measured using any suitable method, including, for example, size exclusion high pressure liquid chromatography, osmolality, nephelometry, differential mobility analysis, sedimentation velocity (analytical ultracentrifugation), light scattering (e.g., Raman spectroscopy), and dialysis.

Definitions

The phrase "pharmaceutically acceptable" is employed herein to refer to those ligands, materials, compositions, and/or dosage forms which are, within the scope of sound medical judgment, suitable for use in contact with the tissues of human beings and animals, substantially non-pyrogenic, without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

An "effective amount" of a salt or excipient of the present invention, with respect to use in a composition comprising a protein-based therapeutic, refers to an amount of the salt or excipient which decreases or eliminates aggregation or increases the stability (e.g., shelf-life) or both of the protein-based therapeutic in the composition.

A "protein-based therapeutic", as used herein, refers to any therapeutic agent which is or comprises a protein or polypeptide, as well as therapeutic compositions in which a protein works as a carrier or targeting agent. Protein-based therapeutics generally can include, without limitation, recombinant proteins, fusion proteins, purified naturally occurring proteins, and polypeptide-containing fragments of any of the foregoing. Some exemplary classes of protein-based therapeutics include, again without limitation, antibodies (including monoclonal antibodies), growth factors, certain hormones, cytokines, antigens, and enzymes. Examples of protein-based therapeutics include, without limitation, factor VII; factor IX; erythropoietin (epoetin alfa; Epogen®; Procrit®); human growth hormone; various colony stimulating factors, such as granulocyte-macrophage colony stimulating factor (GM-CSF; sargramostim; Leukine™) and granulocyte colony stimulating factor (G-CSF; filgrastim, Neupogen®); interferons, such as interferon alpha-2a (e.g., Roferon® A), interferon alpha-2b (e.g., Intron® A), interferon beta-1a (Avonex®), and interferon beta-1b (Betaseron®); interleukins, such as interleukin-2 (IL-2; aldesleukin; Proleukin®); vasopressin; growth hormone releasing factor; relaxin; somatostatin; somatotropin (Nutropin®); insulin; atrial natriuretic factor; glucagon; desmopressin; calcitonin; various angiogenic growth factors, such as vascular endothelial growth factor (VEGF); nerve growth factor (NGF); leuteinizing hormone-releasing hormone (LHRH) analogs; and antibodies. Antibodies include, to name but a few, anti-tumor necrosis factor alpha (anti-TNF-α; adalimumab; Humira®; also infliximab; Remicade®), anti-CD3 (muromonab-CD3; Orthoclone OKT3®), anti-vascular endothelial growth factor A (anti-VEGF-A; bevacizumab; Avastin®), anti-HER/2-neu (trastuzumab; Herceptin®), anti-CD20 (rituximab; Rituxan®; also tositumomab; Bexxar®), anti-IgE (omalizumab; Xolair®), anti-respiratory syncytial virus (anti-RSV; palivizumab; Synagis®), anti-CD25 (basiliximab; Simulect®), anti-epidermal growth factor receptor (anti-EGFR; cetuximab; Erbitux®), and anti-CD33 (gemtuzumab; Mylotarg®). Fusion proteins include, for example, etanercept (Enbrel®). Enzymes include, for example, dornase alfa (Pulmozyme®), tissue plasminogen activator (tPA), glucocerebrosidase (imiglucerase; Cerezyme®), and alpha galactosidase A (agalsidase; Fabrazyme®). Of course, protein-based therapeutics also can include biologically active fragments and derivatives of any of the foregoing protein-based therapeutics.

EXEMPLIFICATION

The invention now being generally described, it will be more readily understood by reference to the following examples which are included merely for purposes of illustration of certain aspects and embodiments of the present invention, and are not intended to limit the invention.

Example 1

Initial Preparation and Characterization of PAMAM Dendrimers

1. Materials

Figure 13:
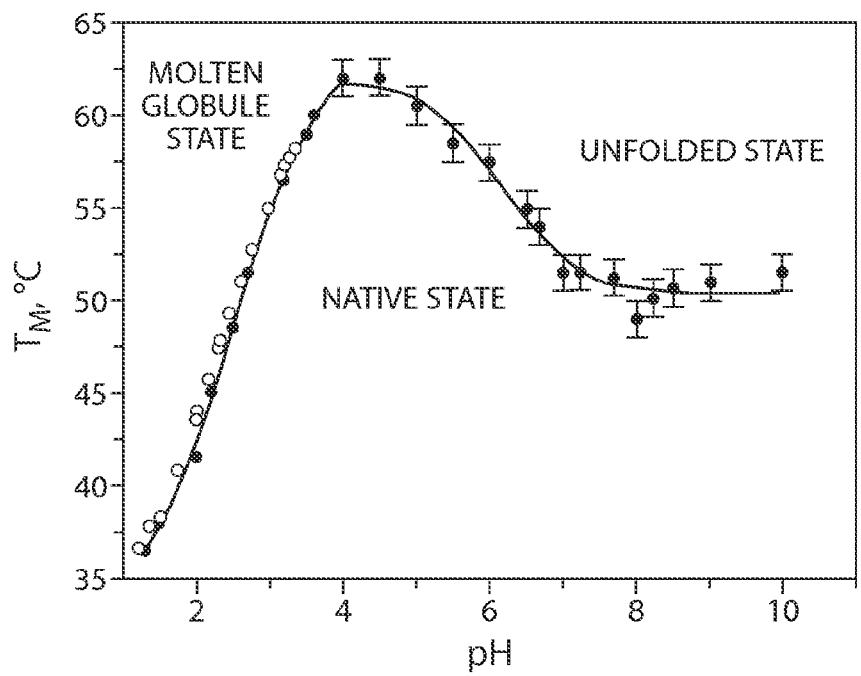
FIG. 13 is a graph depicting denaturation midpoint temperature ($T_m$) versus pH for aCgn, demonstrating optimal conformational stability.
Figure 14:
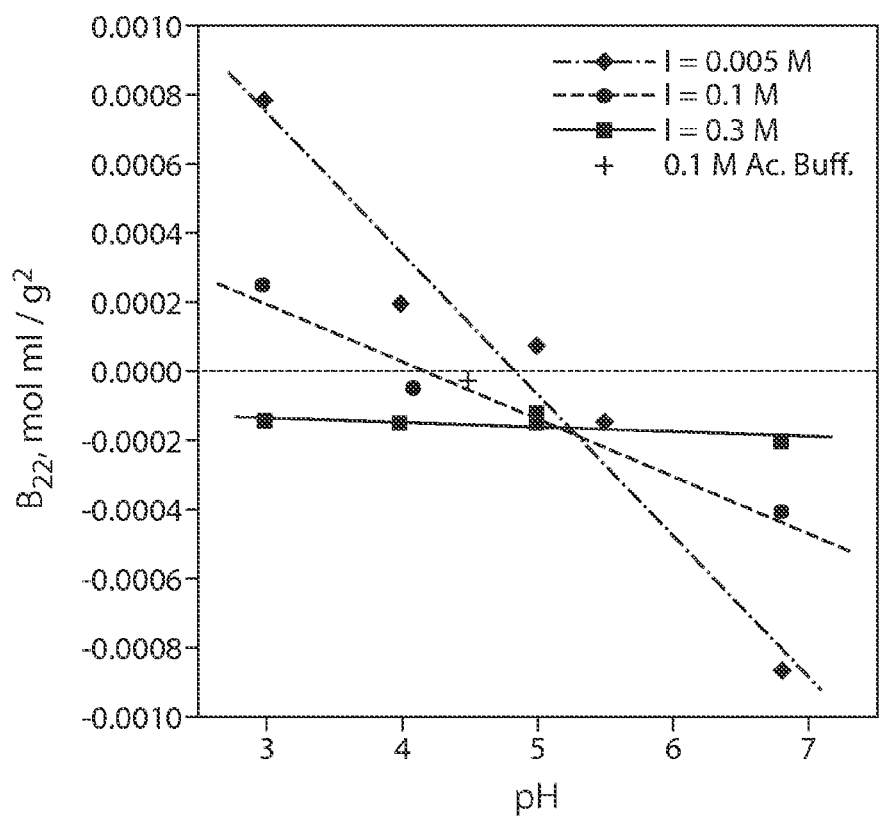
FIG. 14 is a graph depicting Osmotic $2^{nd}$ Virial Coefficient ($B_{22}$) values versus pH and ionic strength for aCgn, demonstrating optimal colloidal stability and that aCgn is least sensitive to ionic strength at pH 5.
Figure 15:
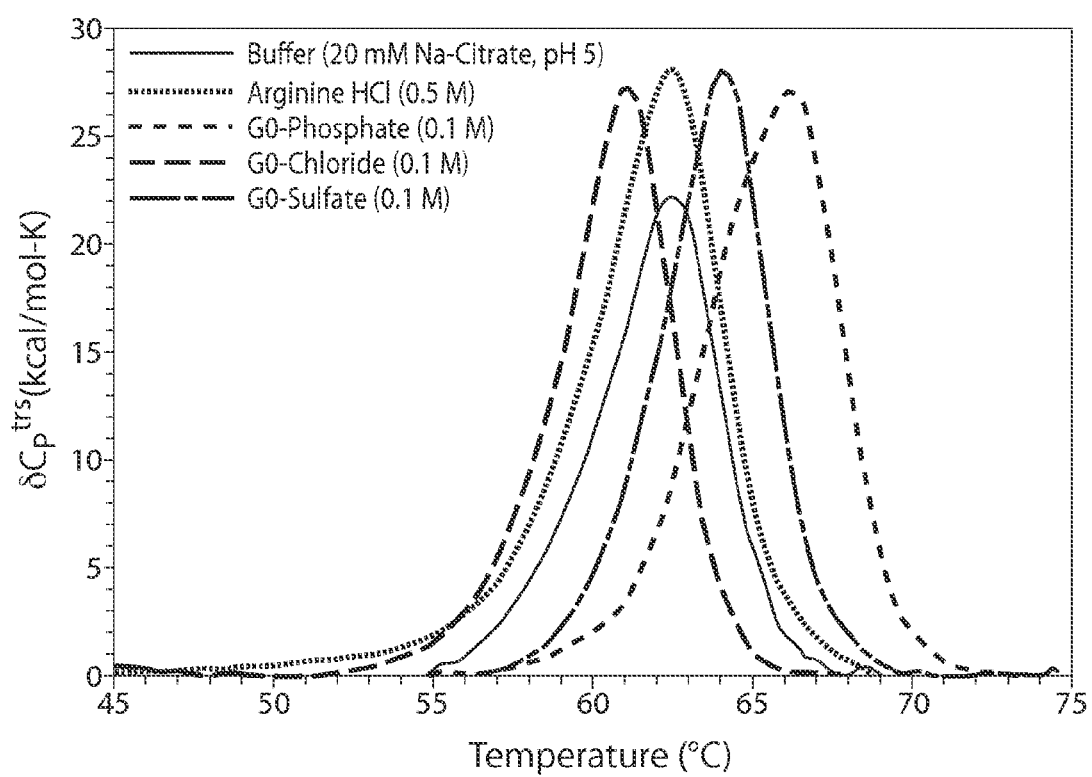
FIG. 15 is a graph depicting thermal stability of the salts along with buffer and Arginine-HCl.

Bovine α-chymotrypsinogen A type II (aCgn) (C4879) was attained from Sigma-Aldrich (St. Louis, Mo.). All other reagents used were also attained from Sigma-Aldrich in the highest available grade. The concentration of aCgn was determined by absorbance using an extinction coefficient of 1.97 mL*$mg^{-1}cm^{-1}$ at 282 nm. No corrections were made for cosolute concentrations or light scattering since the concentrations were typically low due to the protein solutions being diluted with pure water for the purpose of producing a sample with an optical density of about 1.0.

α-Chymotrypsinogen A (aCgn) was selected as a model protein for aggregation because it is a well characterized protein that has been used extensively as a model protein in aggregation studies due to it having aggregation characteristics similar to therapeutically relevant proteins. More importantly, the native state is monomeric, with simple unfolding thermodynamics and kinetics that form non-native aggregates on a reasonable time scale at mildly elevated temperatures.

aCgn is a globular single-domain protein with a molecular mass of 25.7 kDa and an isoelectric point (pI) of 9.2 (thus it has a positive charge when formulated at physiological or low pH). The protein is the inactive precursor of the serine protease chymotrypsin. Thermal stability studies show the protein to be most stable against unfolding at a pH between 4 and 6 (see FIG. 13).

The aggregation of aCgn was accelerated by incubating samples at an elevated temperature. A temperature of 52.5° C. was found to be optimal, in that it was well below the onset of unfolding but accelerated aggregation enough to allow an aggregation experiment to be completed in less than a day. In addition to all aggregation experiments being conducted at that temperature, all samples contained 10 mg/mL aCgn, held at pH 5.0 using a 20 mM sodium citrate buffer. 50 µL aliquots of each protein-cosolute mixture were placed in 0.2 mL polymerase chain reaction (PCR) tubes and then incubated in a Bio-Rad Mycycler thermal cycler with a timer initiated when the thermal cycler reached the desired temperature. Each series contained 12 samples and up to 8 different mixtures were tested at the same time during any given experiment. Samples were removed periodically and immediately placed in an ice bath to quench the aggregation reaction. The length of each experiment was planned so that the extent of reaction was such that at least 20% of the protein aggregated, making changes in the rate of aggregation pronounced. After at least five minutes in the ice bath, the samples were briefly spun in a minicentrifuge to remove precipitated aggregates and then transferred to autosampler vials.

All aCgn samples were first treated with phenylmethylsulfonyl fluoride to inhibit residual amounts of active enzyme and, after dialysis, solutions were frozen, rather than lyophilized, in 0.3 mL aliquots and used within 6 months. Storing the protein in this manner did not seem to have any detrimental effect on the quality of the protein (i.e., the amount of aggregates in the initial solution) or the rate of aggregation when used in the study. Solutions for the aggregation study were prepared by first preparing a solution of the cosolute of interest in a 20 mM sodium citrate pH 5 buffer at a concentration double that of interest (adjusting the pH to 5 if needed with the appropriate acid or an 8 M sodium hydroxide solution), then mixing 0.3 mL of this solution with 0.3 mL of a thawed aCgn solution. This solution was then divided into twelve aliquots, each 50 µL in volume, and incubated at an elevated temperature, as described below.

2. Procedure:

(a) Synthesis

Figure 2:
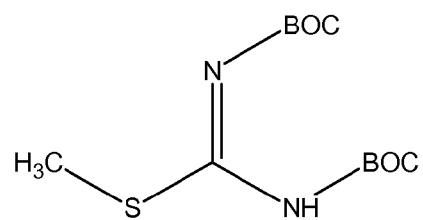
FIG. 2 shows the structure for 1,3-Bis(tert-butoxycarbonyl)-2-methyl-2-thiopseudourea, the guanidinylating agent utilized for the synthesis of the excipients.
Figure 3:
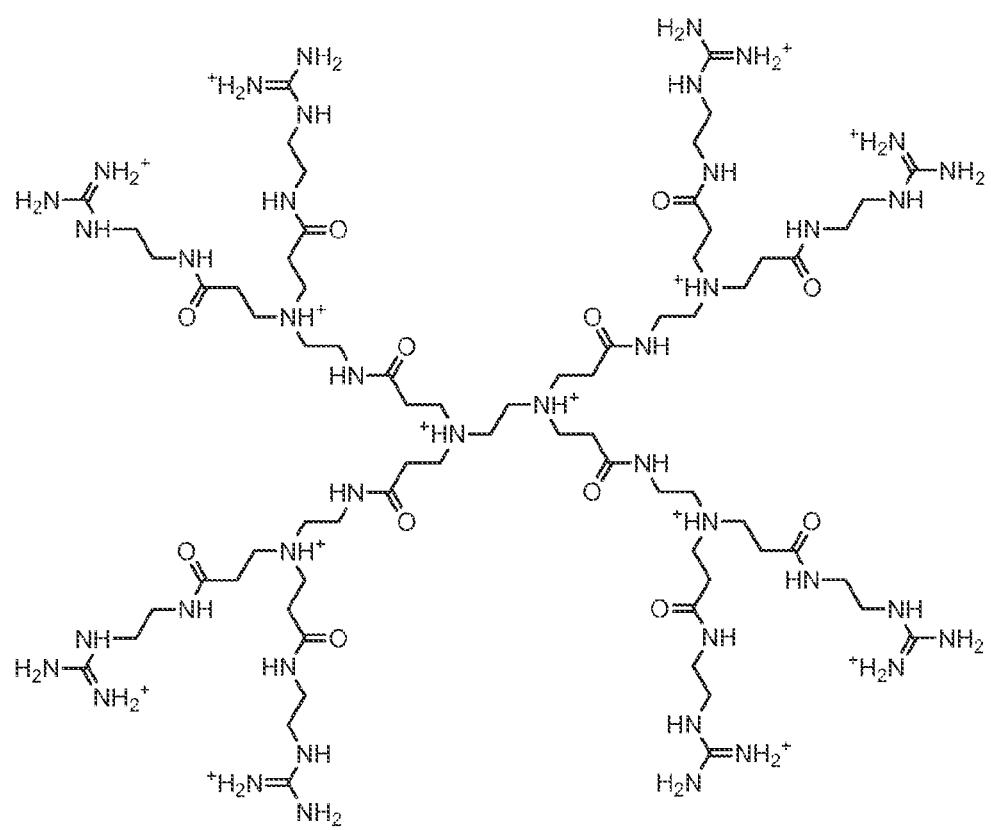
FIG. 3 shows a Generation 1 PAMAM Dendrimer, Ethylene Diamine Core, with Guanidinium Chloride Surface Groups (G1-C1).
Figure 4:
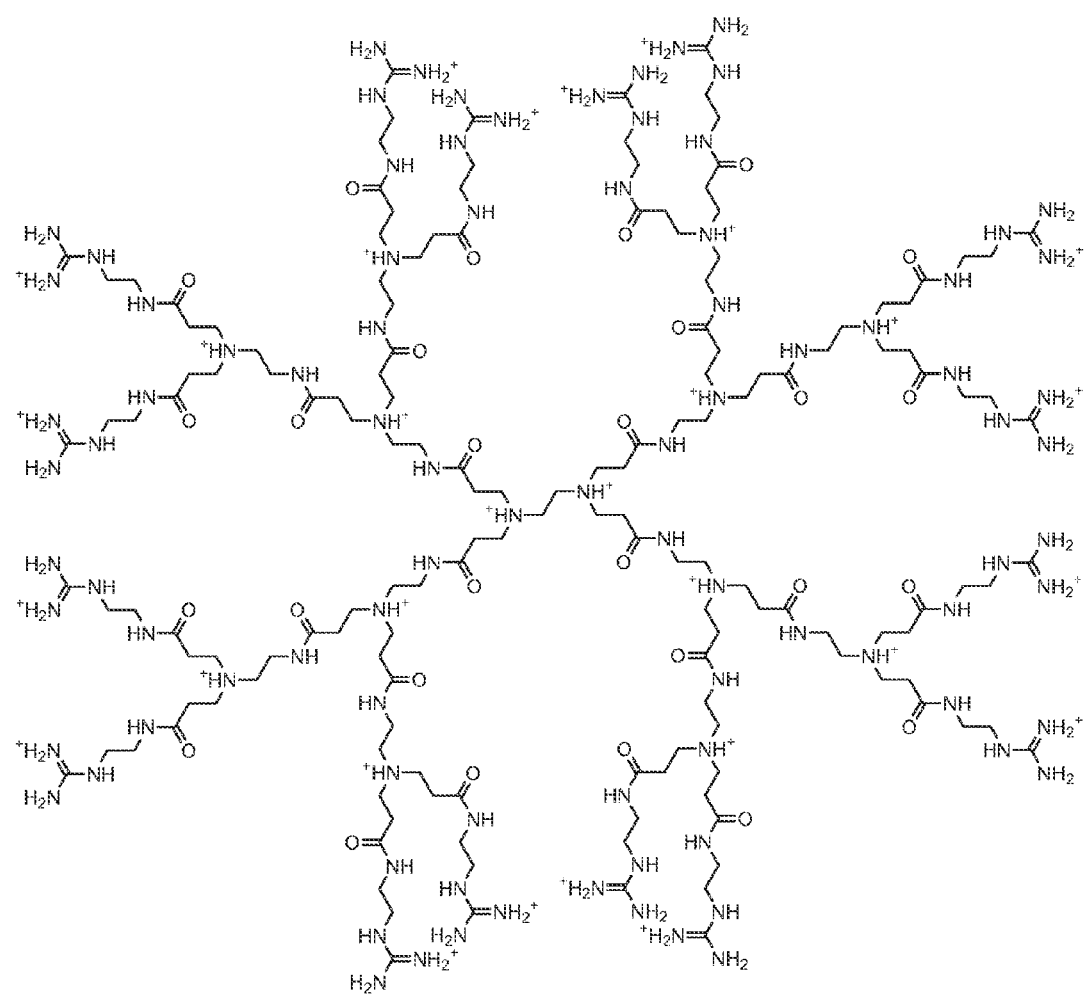
FIG. 4 shows a Generation 2 PAMAM Dendrimer, Ethylene Diamine Core, Guanidinium Chloride Surface Groups (G2-C1).

The general procedure developed for synthesizing the novel excipients involved converting commercially available amines into guanidine compounds through the use of a guanidinylating agent. The synthesis of guanidine compounds has received much attention lately because of the biochemical and pharmaceutical importance of the uanidine moiety and a variety of guanidinylating agents are commercially available. Katritzky and Rogovoy have reviewed the recent developments in guanidinylating agents. Of the many reagents available for different guanidinylation purposes, the most applicable reagents are either a thiopseudourea or a pyrazole carboxamidine because of the desire to synthesize compounds with unsubstituted guanidines on the outer surface of the compound. The latter is a more potent guanidinylating agent but the former allows for an easier purification procedure since the leaving group is a volatile thiol that can simply be evaporated from the solution. Most reagents come with protecting groups on the nitrogens. A tert-butoxycarbonyl (BOC) protecting group was chosen (see FIG. 2) since it allowed for the reaction and purification to be carried out in an organic solvent (an aqueous phase synthesis was not ideally suited due to limited reagents available and limited purification options) and the BOC group is easily removed with a strong acid, such as hydrogen chloride, forming a guanidinium salt, the desired state of the uanidine group.

The procedure developed and presented here is a modification of the method presented by Gers and coworkers. The typical procedure involved adding an excess of the guanidinylation reagent (usually a 1.25-2 fold excess) to a solution containing the amine of interest dissolved in either dichloromethane (DCM) or dimethylformamide (DMF). All reactions were conducted in a fume hood since the methanethiol-produced not only has a very pungent odor, but also it can be toxic in high doses. Reaction vessels were left open to the environment to allow the methanethiol to evaporate from the solution, allowing for a more facile reaction. DCM was found to be advantageous in some cases since it is highly volatile and thus easily removed through evaporation prior to purification. However, the substitution reaction involved proceeds somewhat slowly in DCM and solutions tend to dry out if reaction times are too long, thus it was only used for the smaller excipients, which reacted more quickly due to fewer substitution sites per molecule. DMF is better suited for facilitating the substitution reaction (i.e., reactions proceeded more quickly) and for longer reaction times since it has a lower vapor pressure. However, due to this low vapor pressure, the solvent is somewhat difficult to remove from the solution. Therefore, DMF was only utilized when synthesizing larger excipients.

Solutions were stirred for 8-72 hours with the reaction monitored using thin layer chromatography (TLC). The TLC plates contained a fluorescent dye, allowing for spots containing organic compounds to be detected with a UV lamp. The TLC mobile phase contained a mixture of polar and nonpolar solvents in a ratio that gave the best separation of the reaction system of interest. A typical mixture contained hexane:ethyl acetate:methanol in a ratio of 1.5:1.25:1. Unreacted amine compounds typically had no mobility due to their polar character, while the guanidinylating agent had high mobility due to its nonpolar character. The product (i.e., the excipient of interest with BOC protecting groups) usually had a low to moderate mobility. When all of the amine was consumed by the reaction, the solvent was evaporated under reduced pressure at 60° C. using a rotavap. When DMF was used, only enough solvent was evaporated to reduce the volume to a reasonable level for the purification step.

(b) Purification

Several purification procedures were explored. Initially, a polymer-bound version of the guanidinylating agent was tested since no purification step is required, but such products are expensive and were found to be inefficient at converting all of the substitution sites to guanidine. A liquid-liquid extraction (LLE) technique was also explored, but the best techniques were found to be solid-phase extraction (SPE) (small guanidinium compounds) and precipitation (dendrimers).

For the dendrimer compounds, SPE was found to be ineffective since the dendrimers had a high affinity for the silica and they could not be eluted, even with a highly polar solvent. The dendrimer products were found to be insoluble in hexane due to their polar character. Therefore, after the DMF was evaporated, the residue was dissolved in a minimal amount of diethyl ether and hexane was added to precipitate the product. The guanidinylating reagent is soluble in hexane; thus, after discarding the supernatant, washing the precipitates with hexane, redissolving the precipitates in diethyl ether, and repeating the procedure several times, the product became quite pure.

(c) Deprotection

The deprotection step is quite simple. After purifying the products and evaporating the solvent, the residues were dissolved in a minimal amount of DCM. Then an excess of 2 M HCl dissolved in diethyl ether (sometimes 4 M HCl dissolved in dioxane) was added to the solution. The vials were placed in a fume hood with the cap left open to the environment to allow the carbon dioxide formed to escape. The final product slowly precipitated as the BOC protecting groups were removed. Occasionally, the vials were agitated or stirred with a Teflon-coated spatula. After 24 hours, the precipitates were inspected. The deprotection was assessed to have been completed when the formation of carbon dioxide bubbles had ceased for at least two hours and the precipitates had a hard consistency that was easily ground into a powder (rather than having a consistency similar to syrup or gum). Following the deprotection step, the precipitates were spun down in a centrifuge, the supernatant was discarded, and diethyl ether was added to wash the precipitates. This was repeated at least 8 times (4 washes with diethyl ether and 4 washes with acetone). The precipitates were dried under reduced pressure at 60° C. briefly and then dried under reduced pressure at room temperature for 24-48 hours. The structure of the product was analyzed using mass spectrometry and NMR spectrometry. The purity was analyzed using NMR spectroscopy.

(d) Ion Exchange

Ion exchange was utilized to prepare alternate salt forms of the synthesized excipients. An excess of the sodium salt of interest was used to load the anion of interest onto a column containing Amberlite IRA 400 anion exchange resin. After rinsing the column with HPLC grade water, a solution containing one of the synthesized excipients or L-arginine hydrochloride was passed through the column, in an amount less than half of the capacity of the column and at the recommended flow rate to ensure complete ion exchange. Additional water was then passed through the column to elute all of the excipient.

(e) PAMAM Dendrimers

To summarize, commercially available PAMAM dendrimers (generations 0-2) were guanidinylated with an excess of the guanidinylating agent in DMF. After the reaction was completed, the excess guanidinylating agent was removed by dissolving the reagents in a minimal amount of diethyl ether and precipitating the product with hexane, repeating the procedure until the product was pure (as indicated by TLC). The BOC protecting group was removed from the purified product with concentrated HCl dissolved in either diethyl ether or dioxane. The precipitated product was washed with diethyl ether and acetone and then dried at an elevated temperature and reduced pressure. Using a larger core dendrimer or synthesizing the dendrimers from scratch (possibly using solid phase synthesis techniques) could allow for larger dendrimers with the same number of surface groups.

(f) Characterization Data

NMR and Mass Spectrometry Data:

BOC Protected Guanidine Modified PAMAM Dendrimers

Generation 0 (G0-BOC)

[$^a$CH$_2$$^a$CH$_2$]
($^b$N[$^c$CH$_2$$^d$CH$_2$$^e$CO$^f$NH$^g$CH$_2$$^h$CH$_2$$^i$NH$^j$C($^k$NH$^l$COO$^m$ C($^n$CH$_3$)$_3$)($^k$N$^{l'}$COO$^{m'}$C($^{n'}$CH$_3$)$_3$)]$_2$)$_2$

Purity (NMR): 91.4%

$^1$H-NMR (400 MHz, CDCl$_3$): δ ppm 11.40 (4H, s, k), 8.51 (4H, t, J=5.5 Hz, i), 7.94 (4H, t, J=4.7 Hz, f), 3.50 (8H, q, J=5.7 Hz, h), 3.34 (8H, q, J=5.6 Hz, g), 2.61 (8H, t, J=5.5 Hz, c), 2.35 (4H, s, a), 2.29 (8H, t, J=5.6 Hz, d), 1.433 (36H, s, n'), 1.439 (36H, s, n)

$^{13}$C-NMR (101 MHz, CDCl$_3$): δ ppm 173.3 I, 163.4 (j), 157.0 (l'), 153.1 (l), 83.4 (m), 79.5 (m'), 52.2 (a), 50.5 (c), 40.6 (h), 39.8 (g), 34.3 (d), 28.2 (n'), 28.5 (n)

MS (ESI$^+$): m/z calculated for 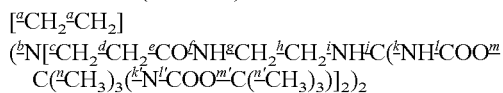 [M+H]+: 1485.90. found: 1485.91 (100%); [M+2H—COOC(CH$_3$)$_3$]$^+$: 1385.85. found: 1385.86 (43%), [M+Na]$^+$: 1507.88. found: 1507.89 (38%).

Generation 1 (G1-BOC)

[$^a$CH$_2$$^a$CH$_2$]—
[$^{b1}$N($^{c1}$CH$_2$$^{d1}$CH$_2$$^{e1}$CO$^{f1}$NH$^{g1}$CH$_2$$^{h1}$CH$_2$$^{b2}$N[$^{c2}$CH$_2$$^{d2}$CH$_2$$^{e2}$ CO$^{f2}$NH$^{g2}$CH$_2$$^{h2}$CH$_2$$^{i}$NH$^{j}$C($^k$NH$^l$C OO$^m$C($^n$CH$_3$)$_3$)($^k$N$^{l'}$ COO$^{m'}$C($^{n'}$CH$_3$)$_3$)]$_2$)$_2$]$_2$

Purity (NMR): 90.6%

$^1$H-NMR (400 MHz, CDCl$_3$): δ ppm 11.37 (8H, s, k), 8.51 (8H, t, J=5.5 Hz, i), 7.95 (8H, t, J=5.3 Hz, f2), 7.69 (4H, t, J=5.4 Hz, f1), 3.49 (16H, q, J=5.6 Hz, h2), 3.33 (16H, q, J=5.4 Hz, g2), 3.18 (8H, q, J=5.7 Hz, g1), 2.65-2.72 (24H, br t, c1+c2), 2.49 (8H, t, J=5.7 Hz, h1), 2.45 (4H, s, a), 2.28-2.31 (24H, br t, d1+d2), 1.43 (72H, s, n'), 1.42 (72H, s, n)

$^{13}$C-NMR (101 MHz, CDCl$_3$): δ ppm 172.8-173.0 (e1+e2), 163.3 (j), 157.0 (l'), 153.1 (l), 83.4 (m), 79.4 (m'), 52.3-52.5 (a+h1), 50.4-50.5 (c1+c2), 40.6 (h2), 40.0 (g2), 37.6 (g1), 34.1-34.2 (d1+d2), 28.2 (n'), 28.5 (n)

MS (ESI): m/z calculated for 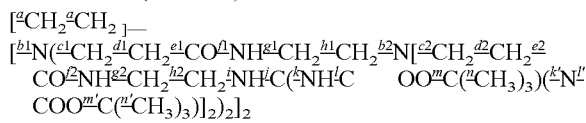 [M+2H]$^{2+}$: 1684.02. found: 1684.54 (100%), [M+3H—COOC(CH$_3$)$_3$]$^{3+}$: 1633.99. found: 1634.52 (97%), [M+Na]$^+$: 1695.51. found: 1695.53 (53%).

Generation 2 (G2-BOC)

[$^{a}$CH$_2$$^{a}$CH$_2$]—($^{b1}$N[$^{c1}$CH$_2$$^{d1}$CH$_2$$^{e1}$CO$^{f1}$NH$^{g1}$CH$_2$$^{h1}$CH$_2$$^{b2}$
N($^{c2}$CH$_2$$^{d2}$CH$_2$$^{e2}$CO$^{f2}$NH$^{g2}$CH$_2$$^{h2}$CH$_2$$^{b3}$N[$^{c3}$CH$_2$$^{d3}$CH$_2$$^{e3}$
CO$^{f3}$NH$^{g3}$CH$_2$$^{h3}$CH$_2$$^{i}$NH$^{j}$C($^{k}$NH$^{l}$COO$^{m}$C($^{n}$CH$_3$)$_3$)
($^{k'}$N$^{l'}$COO$^{m'}$C($^{n'}$CH$_3$)$_3$)]$_2$)$_2$]$_2$)$_2$

Purity (NMR): 94.9%

$^1$H-NMR (400 MHz, CDCl$_3$): δ ppm 11.37 (16H, s, k), 8.51 (16H, t, poorly resolved, i), 7.96 (16H, t, poorly resolved, f3), 7.82 (4H, t, poorly resolved, f1), 7.64 (8H, t, poorly resolved, f2), 3.49 (32H, q, J=4.9 Hz, h3), 3.33 (32H, q, J=4.3 Hz, g2), 3.18-3.21 (24H, br t, g1+g2), 2.65-2.72 (56H, br t, c1+c2+c3), 2.45-2.49 (28H, br m, a+h1+h2), 2.25-2.32 (56H, br t, d1+d2+d3), 1.424 (144H, s, n'), 1.418 (144H, s, n)

$^{13}$C-NMR (101 MHz, CDCl$_3$): δ ppm 172.9-173.1 (e1+e2+e3), 163.3 (j), 157.0 (l'), 153.0 (l), 83.3 (m), 79.4 (m'), 52.4-52.6 (h1), 50.3-50.4 (c1+c2+c3), 40.6 (h3), 40.0 (g1), 37.5-37.6 (g1+g2), 34.1-34.2 (d1+d2+d3), 28.2 (n'), 28.5 (n)

MS (ESI): m/z calculated for C$_{318}$H$_{576}$N$_{90}$O$_{92}$ [M+20H]$^{2+}$: 357.42. found: 357.22 (100%)

Guanidine HCl Modified PAMAM Dendrimers
Generation 0 (G0-Gdn)

[$^{a}$CH$_2$$^{a}$CH$_2$]-($^{b}$NH[$^{c}$CH$_2$$^{d}$CH$_2$$^{e}$CO$^{f}$NH$^{g}$CH$_2$$^{h}$CH$_2$$^{i}$NH$^{j}$C
($^{k}$NH$_2$)$_2$]$_2$)$_2$

Purity (NMR): 77.0%
Yield: 81.8%

$^1$H-NMR (400 MHz, DMSO-d$_6$): δ ppm 11.06 (2H, br s, b), 8.50 (4H, t, J=5.1 Hz, i), 7.89 (4H, t, J=5.2 Hz, f), 7.34 (16H, br s, k), 3.72 (4H, br s, a), 3.43 (8H, t, J=6.3 Hz, c), 3.20-3.24 (16H, br m, g+h), 2.77 (8H, t, J=6.9 Hz, d)

$^{13}$C-NMR (101 MHz, DMSO-d$_6$): δ ppm 169.3 I, 157.3 (j), 49.2 (c), 46.4 (a), 40.1 (g), 38.0 (h), 29.3 (d)

MS (ESI$^+$): m/z calculated for C$_{26}$H$_{62}$N$_{18}$O$_4$Cl$_6$ [M-6HCl+2H]$^{2+}$: 343.24. found: 343.25 (100%); [M-6HCl+3H]$^{3+}$: 229.17. found: 229.17 (59%), [M-6HCl+4H]$^{4+}$: 172.13. found: 172.13 (16%), [M-6HCl+H]+: 685.48. found: 685.51 (4%).

Generation 1 (G1-Gdn)

[$^{a}$CH$_2$$^{a}$CH$_2$]
[$^{b1}$NH($^{c1}$CH$_2$$^{d1}$CH$_2$$^{e1}$CO$^{f1}$NH$^{g1}$CH$_2$$^{h1}$CH$_2$$^{b2}$NH[$^{c2}$CH$_2$$^{d2}$
CH$_2$$^{e2}$CO$^{f2}$NH$^{g2}$CH$_2$$^{h2}$CH$_2$$^{i}$NH$^{j}$C($^{k}$NH$_2$)$_2$]$_2$)$_2$]$_2$

Purity (NMR): 70.4%
Yield: 78.5%

$^1$H-NMR (400 MHz, DMSO-d$_6$): δ ppm 11.09 (2H, br s, b1), 10.45 (4H, br s, b2), 8.67 (4H, t, poorly resolved, f1), 8.51 (8H, t, poorly resolved, i), 7.91 (8H, t, poorly resolved, f2), 7.36 (32H, br s, k), 3.73 (4H, br s, a), 3.45-3.53 (8H, br q, g1), 3.35-3.45 (24H, br t, c1+c2), 3.18-3.27 (40H, br m, h1+h2+g2), 2.71-2.85 (24H, br t, d1+d2)

$^{13}$C-NMR (101 MHz, DMSO-d$_6$): δ ppm 169.5-169.6 (e1+e2), 157.3 (j), 51.3 (h1), 48.7-48.8 (c1+c2), 46.5 (a), 40.2 (g2), 38.1 (h2), 33.7 (g1), 29.1-29.3 (d1+d2)

MS (ESI): m/z calculated for C$_{70}$H$_{158}$N$_{42}$O$_{12}$Cl$_{14}$ [M-14HCl+6H]$^{6+}$: 295.21. found: 295.21 (100%), [M-14HCl+5H]$^{5+}$: 354.05. found: 354.06 (90%), [M-14HCl+4H]$^{4+}$: 442.31; found: 442.32 (70%), [M-14HCl+7H]$^{7+}$: 253.18. found: 253.18 (62%), [M-14HCl+3H]$^{3+}$: 589.41. found: 589.43 (27%).

Generation 2 (G2-Gdn)

[$^{a}$CH$_2$$^{a}$CH$_2$]
($^{b1}$NH[$^{c1}$CH$_2$$^{d1}$CH$_2$$^{e1}$CO$^{f1}$NH$^{g1}$CH$_2$$^{b2}$NH($^{c2}$CH$_2$$^{d2}$CH$_2$$^{e2}$
CO$^{f2}$NH$^{g2}$CH$_2$$^{h2}$CH$_2$ $^{b3}$NH[$^{c3}$CH$_2$$^{d3}$CH$_2$$^{e3}$CO$^{f3}$NH$^{g3}$
CH$_2$$^{h3}$CH$_2$$^{i}$NH$^{j}$C($^{k}$NH$_2$)$_2$]$_2$)$_2$]$_2$)$_2$

Purity: 77.7%
Yield: 81.1%

$^1$H-NMR (400 MHz, DMSO-d$_6$): δ ppm 11.09 (2H, br s, b1), 10.40-10.44 (12H, br s, b2+b3), 8.62-8.69 (12H, br t, f1+f2), 8.51 (16H, t, poorly resolved, i), 7.91 (16H, br t, poorly resolved, f3), 7.34 (64H, br s, k), 3.65-3.75 (20H, br m, a+h2), 3.48-3.53 (24H, br q, g1+g2), 3.35-3.48 (56H, br t, c1+c2+c3), 3.18-3.27 (72H, br m, h1+h3+g1), 2.71-2.82 (56H, br t, d1+d2+d3)

$^{13}$C-NMR (101 MHz, DMSO-d$_6$): δ ppm 169.5-169.7 (e1+e2+e3), 157.3 (j), 51.3-51.4 (h1+h2), 48.7-48.8 (c1+c2+c3), 46.6 (a), 40.2 (g1), 38.1 (h3), 33.7-33.8 (g1+g2), 29.1-29.3 (d1+d2+d3)

MS (ESI$^+$): m/z calculated for C$_{158}$H$_{350}$N$_{90}$O$_{28}$Cl$_{30}$ [M-29HCl+11H]$^{11+}$: 361.25. found: 361.26 (100%); [M-30HCl+8H]$^{8+}$: 492.11. found: 492.11 (97%), [M-30HCl+9H]$^{9+}$: 437.54. found: 437.54 (92%), [M-30HCl+10H]$^{10+}$: 393.89. found: 393.88 (47%), [M-30HCl+7H]$^{7+}$: 562.27. found: 562.27 (33%), [M-30HCl+6H]$^{6+}$: 655.81. found: 655.81 (10%).

2. Results

It was determined that if the chloride ion was exchanged with phosphate, sulfate, or acetate, conformational destabilization would be reduced and aggregation suppression would be enhanced as a result. The solubility of the dendrimers is not reduced by either sulfate or phosphate. The performance of the dendrimer excipients in the form of other salt types is significantly different from the chloride salt form. Exchanging the chloride ion with acetate moderately improves the performance of the generation 0 dendrimer (see FIG. 5).

Figure 5:
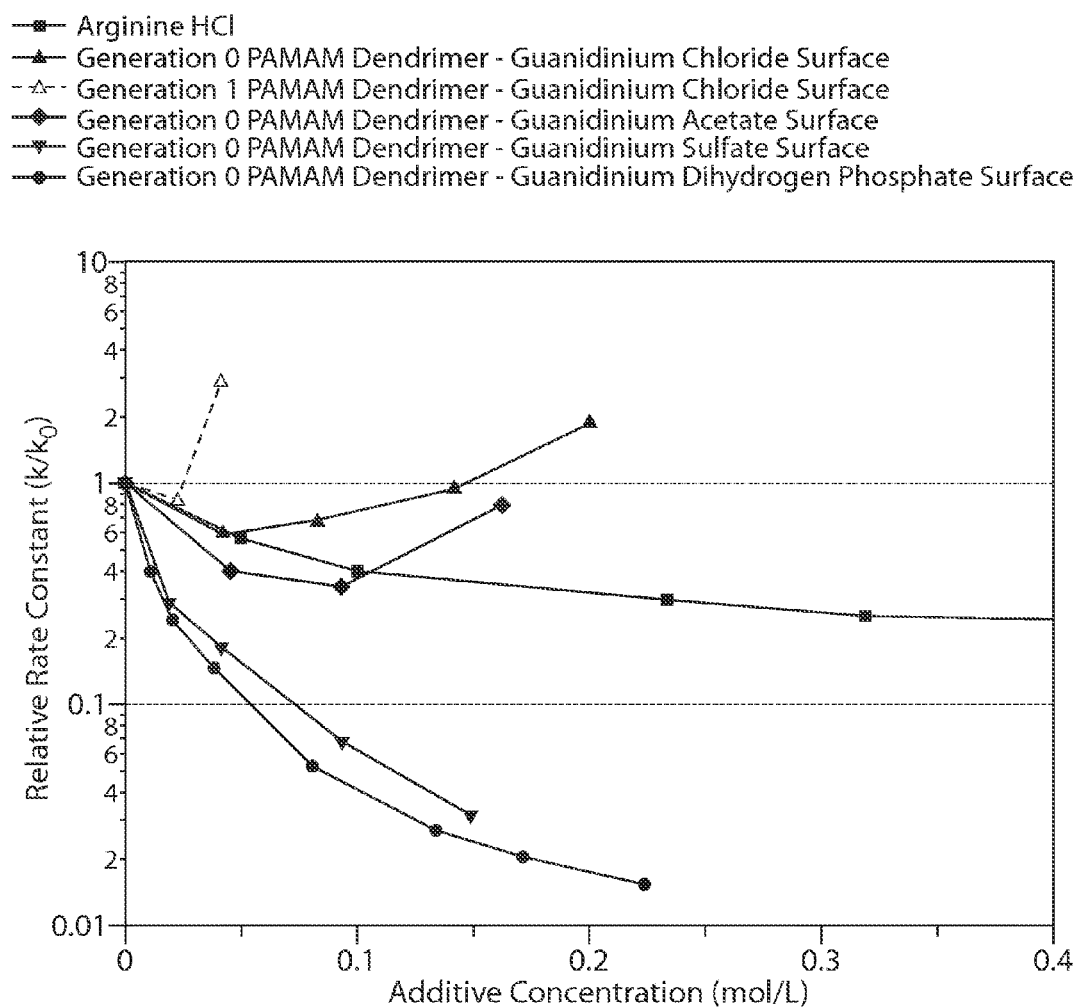
FIG. 5 is a graph depicting the influence of guanidinium modified PAMAM dendrimer salts on α-chymotrypsinogen (aCgn) monomer loss due to aggregation at 52.5° C. All solutions contained 10 mg/mL aCgn and were prepared in a 20 mM sodium citrate pH 5 buffer. The Figure depicts the Relative Rate Constant (as determined by the amount of time for 20% monomer loss) versus additive concentration, with lines drawn through the plots to aid the reader.
Figure 6:
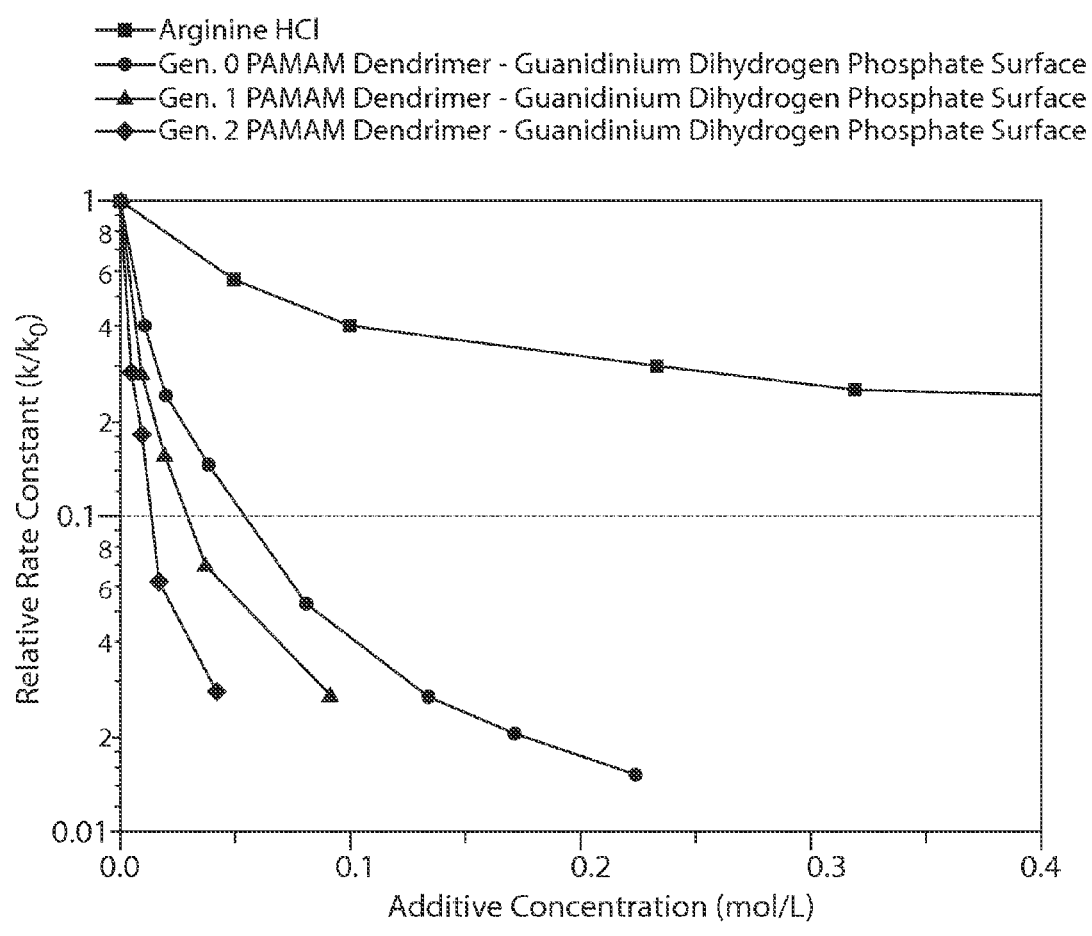
FIG. 6 is a graph depicting the influence of modified PAMAM dendrimers (guanidinium phosphate monobasic surface) on aCgn monomer loss due to aggregation at 52.5° C. All solutions contained 10 mg/mL aCgn and were prepared in a 20 mM sodium citrate pH 5 buffer. The Figure depicts the Relative Rate Constant (as determined by the amount of time for 20% monomer loss) versus additive concentration, with lines drawn through the plots to aid the reader.

When the chloride ion is exchanged with either SO$_4$$^{2-}$ or H$_2$PO$_4$$^-$, the performance of the dendrimers is significantly improved. As shown in FIG. 5, at low concentrations, both the sulfate and phosphate salt forms lower the rate of aggregation to a greater extent than either the chloride or acetate salt forms. Furthermore, as the concentration increases, this trend continues but begins to plateau at a concentration near 0.2 M. At such a concentration, the relative rate constant is approximately 0.02, which is an order of magnitude better than the relative rate constant for arginine. This trend continues for larger dendrimer forms; in fact, the larger dendrimers outperform the generation 0 dendrimer. As shown in FIG. 6, the relative rate constant profiles for the generation 1 and generation 2 phosphate dendrimers are similar to the profile for the generation 0 dendrimer, but the relative rate constant is lower for all concentrations, with the generation 2 dendrimer exhibiting the lower relative rate constant profile.

3. Analysis (a) Nuclear Magnetic Resonance (NMR) Spectrometry

The structure and purity of the synthesized excipients were analyzed via NMR spectrometry. The Bruker Avance 400 NMR spectrometer in the Department of Chemistry Instrumentation Facility (DCIF) was utilized for this purpose. 1D $^1$H (400 MHz) and 1D $^{13}$C (101 MHz) spectrums were produced for official validation of the structure. 2D $^1$H—$^1$H COSY and 2D $^1$H-$^{13}$C HSQC techniques were utilized to help deconvolute the 1D spectra. If any ambiguity persisted, results were compared to predictions made using ChemBioDraw Ultra 12.0. The guanidinylating agent and amine precursors were analyzed as well (which also included the amine in an ammonium chloride salt form for comparison to the guanidinium salt spectrum) to identify any unreacted precursors. The amine starting compounds and the BOC protected intermediates were each dissolved in deuterated chloroform (CDCl$_3$) and the guanidinium salt products and ammonium salt precursors were dissolved in deuterated dimethyl sulfoxide (DMSO-d6), all at a concentration around 25 mg/mL. $^1$H and $^{13}$C spectra were calibrated using residual protio-solvent. The total integrated area of the $^1$H spectra were set to the total number of hydrogens present on the molecule. No unreacted amine or guanidinylating agent were identified, thus the only impurities were residual solvent, which was identified by comparing chemical shift values with literature values. The residual solvent peaks were integrated individually and separate from the product peaks to determine moles of solvent per mole of product, thus allowing a calculation of mass percentage.

(b) Mass Spectrometry (MS)

Several ionization sources were available for mass spectrometry analysis, but electrospray ionization (ESI) was deemed best suited to analyze the synthesized compounds since (1) the technique allows for the analysis of samples with a molecular weight greater than 1000 daltons and (2) of the techniques available for ionizing large compounds, ESI produces the least amount of fragmentation without the use of a matrix, which can interfere with the analysis of ions with small mass-to-charge ratios. The DCIF houses a Bruker Daltonics APEXIV 4.7 Tesla Fourier Transform Ion Cyclotron Resonance Mass Spectrometer (FT-ICR-MS) equipped with an electrospray ionization source. Only positive ions were analyzed (with samples processed by the facility's mass spectrometry specialist) and the data was deemed satisfactory when the major peaks corresponded to a $[M+nH]^{n+}$ value, typical of ESI-MS.

(c) Size Exclusion HPLC (SE-HPLC)

15 µL, of each aCgn sample were injected into an Agilent 1200 series HPLC, equipped with a Zorbax GF-250 (4.6×250 mm, 4 micron) size exclusion column and a UV-Vis detector, during a sequence. The HPLC mobile phase contained 25 mM citric acid monohydrate, 25 mM sodium acetate, and 200 mM sodium chloride with the pH adjusted to 4.0 using sodium hydroxide. The flow rate was set at 1 mL/min and samples were monitored at 280 nm.

Most of the aggregates that formed either precipitated or did not pass through the column, thus only the monomer concentration was monitored with time. Peak area at each time point was compared to the peak area for an unstressed sample to create a monomer loss profile normalized with respect to the initial concentration. Each profile was compared to a profile for a sample containing no cosolute to determine the change in aggregation rate upon addition of the cosolute. For a control, each aggregation experimental setup had one protein solution that contained no cosolute to verify that the baseline aggregation rate remained constant amongst all experiments. For all aCgn concentrations studied, the aggregation exhibited $2^{nd}$ order kinetics, thus rate constants were determined by fitting each data set to a $2^{nd}$ order rate law.

(d) Cosolute Osmotic Virial Coefficient Measurements

Vapor pressure osmometry was utilized to evaluate intermolecular interactions in aqueous solutions of the arginine salts. The most frequently used approach to describe interactions in electrolyte solutions is the ion interaction or virial coefficient model developed by Pitzer and co-workers. The model accounts for nonideal trends in the osmotic coefficient, $\phi$, which is defined as $$\phi = -\frac{\ln a_w}{vmM_w} = \frac{Osm}{vm}$$

where $a_w$ is the activity of water, $M_w$ is the molar mass of water, m is the solute molality, and v is the stoichiometric coefficient of the solute. For a single MX electrolyte solution, the Pitzer model can be expressed as $$\phi - 1 = |z_M z_X| f^\phi + \frac{2v_M v_X}{v} B^\phi m + \frac{2(v_M v_X)^{3/2}}{v} C^\phi m^2$$

where $v_M$ and $v_X$ are the number of M and X ions in the formula and $z_M$ and $z_X$ are their respective charges in electronic units; also $v=v_M+v_X$. The other parameters have the form $$f^\phi = -A_\phi \left[ \frac{I^{1/2}}{1+bI^{1/2}} \right]$$

$$B^\phi = \beta^{(0)} + \beta^{(1)} e^{-\alpha I^{1/2}}$$

where I is the ionic strength and $A_\phi$ is the Debye-Hückel coefficient for the osmotic coefficient, both in the molal concentration scale. The Wescor 5520 vapor pressure osmometer utilized in this study has no temperature control, but $A_\phi$ is a relatively weak function of temperature, thus the value for water at the standard temperature of 25° C. was utilized, which is $A_\phi=0.392$ $(kg/mol)^{1/2}$. The parameters $\alpha$ and b can be floated during analysis but they are typically fixed at 2.0 $(kg/mol)^{1/2}$ and 1.2 $(kg/mol)^{1/2}$, respectively, for all electrolytes. A previous analysis of ArgHCl utilized these parameter values and thus, the same was done in this study. The parameters $\beta^{(0)}$ and $\beta^{(1)}$ describe the ionic strength dependence of the second osmotic virial coefficient, $B^\phi$, which describes short range binary interactions. $C^\phi$ is the third virial coefficient, which describes ternary interactions and is typically small and only important at high concentrations.

In this analysis, the arginine salts were dissolved in HPLC grade water, with no buffering component or pH adjustment. A series of samples were prepared gravimetrically and the density of each solution was determined using an Anton Paar DMA 4500 density meter, accurate to within $1\times10^{-5}$ g/mL, to determine both the molar concentration of each solution and the partial molar volume. $\beta^{(0)}$, $\beta^{(1)}$ and $C^\phi$ were determined by fitting the osmometry data to $$\phi - 1 = |z_M z_X| f^\phi + \frac{2v_M v_X}{v} B^\phi m + \frac{2(v_M v_X)^{3/2}}{v} C^\phi m^2$$

using the nonlinear fitting program Igor Pro.

(e) Preferential Interaction Determination—Dialysis/Densimetry

Density measurements were carried out according to the previously described procedure. Lyophilized protein was dried in a desiccator at room temperature for 2 days under reduced pressure to remove trace amounts of water. Five samples of the dried protein were dissolved at a concentration ranging from 5 to 25 mg/mL in 4 mL of buffer solutions containing the cosolute at the desired concentration and pH. For the constant molality measurements, 2 mL of each sample were set aside, tightly sealed, and left at room temperature overnight prior to the densimetry measurements. In the constant chemical potential experiments, the other 2 mL of each protein sample were transferred to a dialysis bag and dialyzed at room temperature for 48 hours against two changes of solvent (400-500 mL each) prior to densimetry measurements. The density of each solution was measured using an Anton Paar DMA 4500 density meter, accurate to within 0.00001 g/mL. After the density measurements, samples of each protein solution were diluted gravimetrically with water to a final optical density of about 1.0 and the concentrations were determined spectrophotometrically with a PerkinElmer Lambda 35 UV/Vis spectrometer. The partial specific volume of the protein from each experiment was determined using:

$$\phi_2^\circ \equiv \lim_{C_2 \to 0} \phi_2 = \lim_{C_2 \to 0} \left[ \frac{1}{\rho_s^\circ}\left(1 - \frac{\rho - \rho_s^\circ}{C_2}\right)\right],$$

and these values were used to compute the preferential interaction coefficient via $$\Gamma_{\mu_1, \mu_3} = \frac{M_2}{M_3}\left(\frac{\phi_2^\circ - \phi_2'^\circ}{1/\rho_s^\circ - \bar{v}_3}\right).$$

(f) Preferential Interaction Determination—Vapor Pressure Osmometry (VPO)

Osmolality measurements were carried out according to the previously described procedure. For improved accuracy, all samples were prepared gravimetrically using a Mettler Toledo balance with a precision of 0.1 mg. Partial molar volume values of the
cosolutes (evaluated using and density values of the $$\bar{v}_3 = \frac{1}{\rho_s^\circ} + (1-z_3)\left(\frac{\partial(1/\rho_s^\circ)}{\partial z_3}\right)_{T,P,z_2=0}$$

and density values of the solutions were used to determine concentration. Though a three component system was utilized to derive equations it $$\Gamma_{\mu_3}^I \cong \frac{m_3}{m_2}\left[1 - \frac{\Omega_3}{\Omega_3^{\circ(2)}}\right] \text{ and } \Gamma_{\mu_3}^{II} \cong \left[\frac{m_3(\Omega_2^{\circ(3)} + \Gamma_{\mu_1}\Omega_3)}{m_3\Omega_3 + m_2(\Omega_2^{\circ(3)} + \Gamma_{\mu_1}\Omega_3)}\right],$$

it was found that a pH buffering salt was necessary for the measurements, mainly to stabilize the protein solution and to control the pH of the guanidine HCl and arginine HCl solutions. Since the concentration of the buffering salt is constant for every sample, not to mention low, it has no contribution to the computed slopes used in Eqs.

$$\Gamma_{\mu_3}^I \cong \frac{m_3}{m_2}\left[1 - \frac{\Omega_3}{\Omega_3^{\circ(2)}}\right] \text{ and } \Gamma_{\mu_3}^{II} \cong \left[\frac{m_3(\Omega_2^{\circ(3)} + \Gamma_{\mu_1}\Omega_3)}{m_3\Omega_3 + m_2(\Omega_2^{\circ(3)} + \Gamma_{\mu_1}\Omega_3)}\right].$$

Therefore, the molal concentration of the buffer can be lumped together with that of the water, thus the system can still be treated as a three-component system (i.e., solvent, protein, and additive).

Stock solutions of both BSA and lysozyme and stock solutions of the cosolutes were each prepared in a 40 mM sodium phosphate buffer, pH 6.0 (aCgn measurements were conducted in 20 mM sodium citrate buffer, pH 3.5 or pH 5.0). Stock solutions of the cosolutes were used so that a series of samples could be easily produced with varying solute concentrations by dilution with water and buffer. The protein stock solutions were further purified by placing the solutions under dialysis for 48 hours at room temperature against two changes of buffer (1 L each). To obtain the best possible results from the VPO measurements, the protein solutions were concentrated to within 100-200 mg/mL (depending on the solubility of the protein) using Amicon Ultra centrifugal filter tubes. To determine the concentration, samples of each stock solution were diluted gravimetrically with water to a final optical density of about 1.0 and the concentration determined spectrophotometrically with a PerkinElmer Lambda 35 UV/Vis spectrometer. It should be noted that the protein stock solutions were stored at 4° C. and used within one week of their preparation.

Equations $\Gamma_{\mu_3}^I \cong \frac{m_3}{m_2}\left[1 - \frac{\Omega_3}{\Omega_3^{\circ(2)}}\right]$ and $\Gamma_{\mu_3}^{II} \cong \left[\frac{m_3(\Omega_2^{\circ(3)} + \Gamma_{\mu_1}\Omega_3)}{m_3\Omega_3 + m_2(\Omega_2^{\circ(3)} + \Gamma_{\mu_1}\Omega_3)}\right]$ require that osmolality measurements for the three component solution at various cosolute concentrations be taken at a constant protein molal concentration. However, it is difficult to prepare such solutions, and therefore samples with a constant molar volume were prepared instead. To correct for this, a relationship between constant protein molal concentration (m2) and constant protein molar concentration, derived elsewhere, is used to obtain values for the desired parameter:

$$\Omega_3 = \frac{(\partial Osm/\partial m_3)_{[2]}}{1 - \Gamma_{\mu_1}\left(\frac{[2]\bar{V}_3}{1 - [2]\bar{V}_2}\right)}$$

A Wescor Vapro® vapor pressure osmometer (model 5520) was used for all osmometry measurements. The instrument was calibrated using 0.1, 0.29, and 1 mol/kg osmolality standards provided by Wescor. Due to slight drifts in the calibration points, the instrument was recalibrated after every four measurements and the thermocouple was cleaned daily using concentrated ammonium hydroxide followed by a rinse with HPLC grade water. Even though the instrument is designed to measure osmolality readings as high as 3.2 mol/kg, the accuracy of measurements above the last calibration point of 1 mol/kg is significantly impaired from extrapolating the calibration curve and increased system noise at high solute concentrations. It was discovered during the course of such measurements that this error significantly influenced the accuracy of the results. Therefore, cosolute concentration was limited so that all measurements had an osmolality less than 1.2 mol/kg. The data sets for each cosolute included at least 16 individually made solutions (both for the sets with and without the protein). Each sample contained approximately 80 µL of solution (40 µL of diluted cosolute stock solution and 40 µL of the protein stock solution). A minimum of three measurements on each solution were made. If the standard deviation for a particular solution was greater than 2 mmol/kg, more measurements were taken or another sample was prepared. For a given solute, data representing the dependence of osmolality on solute molality were fitted by a quadratic equation, with all fitting parameters floated. Data were weighted by the standard deviation of the individual osmolality measurements for the same solution using the nonlinear fitting program Igor Pro. Using a cubic function or other fitting curves did not improve the fitting for any of the data.

(g) Preferential Interaction Determination—Determination of the Isoosmolal
Preferential Interaction Coefficient ($\Gamma_{\mu_1}$)

Though the isoosmolal preferential interaction coefficient $\Gamma_{\mu_1}$ can be determined directly from osmolality $$\left(\text{via } \Gamma_{\mu_1} = -\frac{\Omega_2}{\Omega_3}\right),$$

it is difficult to obtain an accurate measure of the relationship between osmolality and protein concentration for every cosolute concentration. This is mainly due to the fact that osmolality does not change significantly over the available range of protein concentration. However, it can be approximated by comparing the molal concentration of the cosolute in the protein solution ($m_3$) to that in a two-component solution at the same osmolality (i.e., the same water chemical potential) ($m_3^\Delta$).

$$\Gamma_{\mu_1} = \left(\frac{\partial m_3}{\partial m_2}\right)_{T,P,\mu_1} \cong \frac{(m_3 - m_3^\Delta)}{m_2}.$$

By using such a procedure, the preferential interaction coefficient $\delta_{\mu_3}$ can be determined using both approximation methods from just three series of samples, a series containing all three components at various cosolute concentrations, a series of just protein and buffer at various protein concentrations, and a series of just the cosolute and buffer at various cosolute concentrations.

(h) Folding Thermodynamics/Structure Analysis—Differential Scanning Calorimetry (DSC)

The thermodynamic stability of aCgn in the presence of the arginine salts was determined by DSC (Microcal VP-Differential Scanning calorimeter located in the Biophysical Instrumentation Facility (BIF) at MIT). Each reading began with a minimum of three buffer-buffer up and down scans (in this case, the buffer also contains the cosolute of interest) to establish a reproducible thermal history followed by a single protein-buffer up scan. aCgn was analyzed at a concentration of 1 mg/mL in a 20 mM sodium citrate pH 5 buffer containing the cosolute of interest and a scan rate of 90° C./hour. The data was analyzed in the MicroCal Origin® plotting software. In the analysis, the last buffer-buffer reference scan was first subtracted from the data and then the data was normalized with respect to the protein concentration, cell volume, and scan rate. The baseline (which was progressed through the peak) was then subtracted from the plot and the denaturation midpoint temperature, $T_m$, was taken as the temperature at the peak maximum of the unfolding event. For each arginine salt, three concentrations (including zero concentration) were tested and $T_m$ values with respect to cosolute concentration were fitted to a linear trend.

Example 2

Aggregation Suppression

Having now described initial characterization of certain PAMAM dendrimers in Example 1, this example describes aggregation in more detail.

Figure 7:
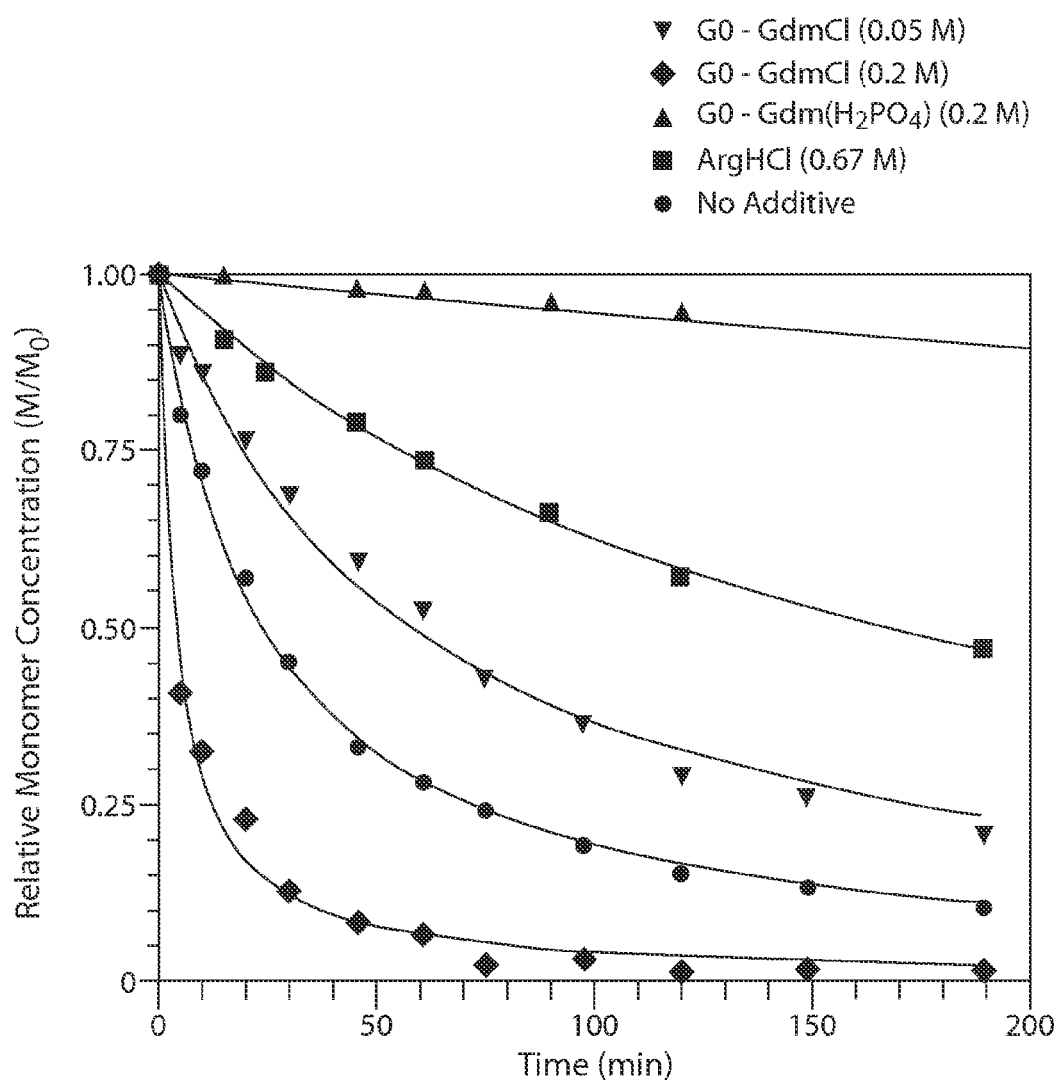
FIG. 7 is a graph depicting monomer loss profiles for solutions containing Generation 0 PAMAM dendrimers with guanidinium chloride or $H_2PO_4$ surfaces at varying concentrations.
Figure 8:
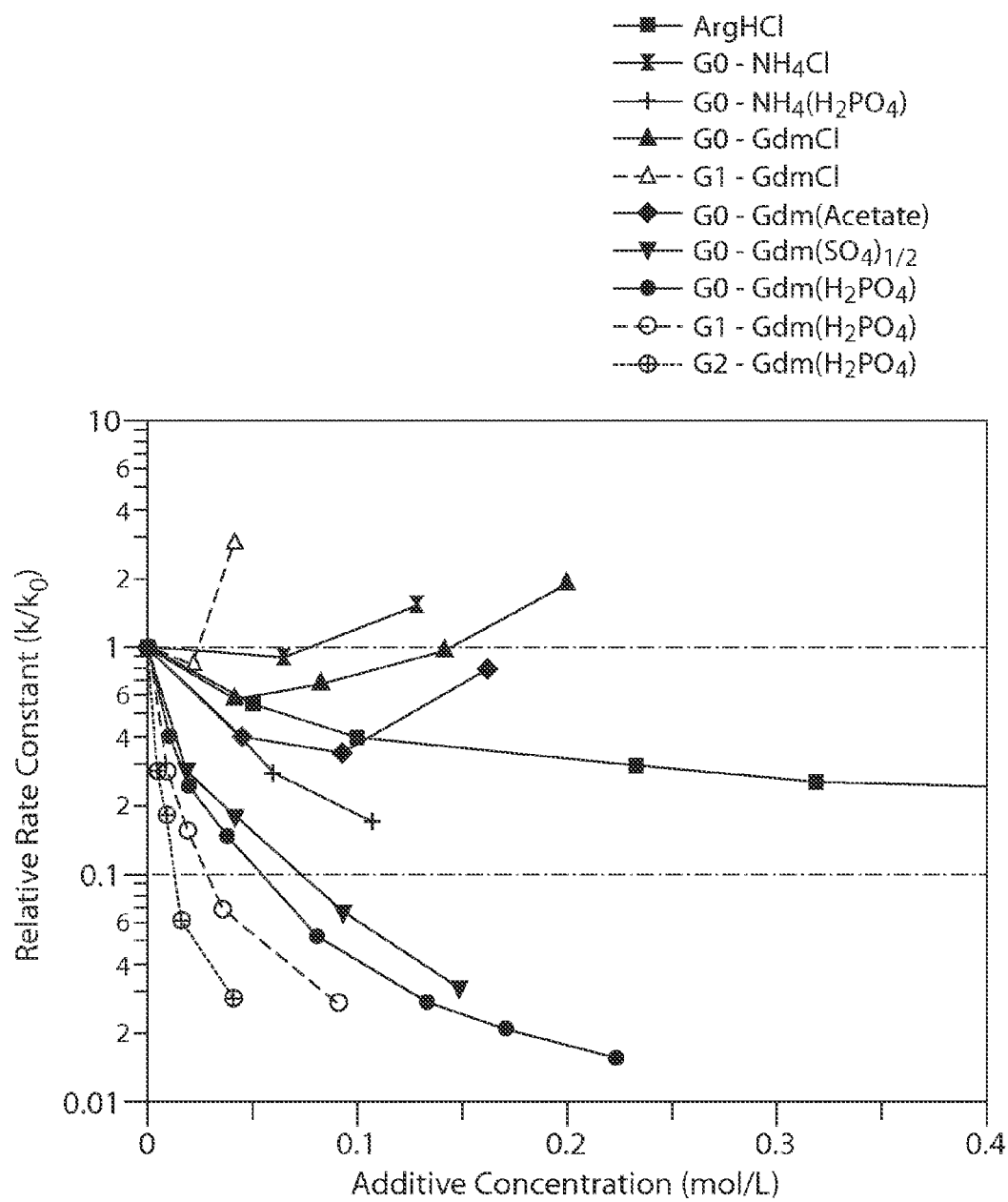
FIG. 8 is a graph depicting rate constant, k, for aCgn monomer loss relative to the rate constant for no additive, $k_0$, versus additive concentration.

The most notable consequence of perturbing a protein's environment is the enhancement or inhibition of protein aggregation. Deyoung L R et al. (1993) Accounts Chem Res 26:614-620; Fink A L (1998) Fold Des 3:R9-R23. The guanidinium-modified dendrimers were added to model protein solutions and incubated at an elevated temperature to determine how they influence the rate of this degradation pathway. FIG. 7 shows α-chymotrypsinogen A (aCgn) monomer loss profiles, as determined by size exclusion HPLC, for solutions containing a generation 0 PAMAM dendrimer with the surface modified to GdmCl. At low dendrimer concentrations (0.05 M), the rate of monomer loss in the presence of the surface-modified dendrimer is slower than when compared to the reference solution. However, this aggregation rate reduction is insignificant when compared to the rate reduction induced by a high concentration of other commonly used additives such as arginine hydrochloride (ArgHCl), which is also depicted in the figure. Furthermore, as the concentration of the surface-modified dendrimer is increased, the aggregation rate reduction decreases until ultimately, the rate of aggregation is increased. At a concentration of 0.2 M, the surface-modified dendrimer induced rapid aggregation, causing a 50% loss in about 10 minutes as opposed to 30 minutes for the solution containing no cosolute. These results only become worse for higher generations. As shown in FIG. 8, the rate of monomer loss for the generation 1 dendrimer with a surface modified to GdmCl indicates a large increase in the rate of aggregation at concentrations as low as 0.05 M, even though at lower concentrations the compound inhibited aggregation by a moderate amount.

These results are comparable to other large compounds with surfaces modified to Gdm, which exhibit a strong interaction with proteins that results in destabilization at moderate to high concentrations. Giehm L et al. (2008) Biopolymers 89:522-529; Okuro K et al. (2009) J Am Chem Soc 131:1626-1627. However, a previous inquiry into various arginine salts showed that the interaction between a Gdm functional group and a protein is strongly influenced by the counterion to the Gdm moiety. Schneider C P et al. (2011) J Phys Chem B 115:7447-7458. The reason for this is that hydrogen bond accepting anions will tend to form strong hydrogen bonds with the hydrogen bond donating Gdm group. Thus the interaction between the modified dendrimers and the protein can be altered by exchanging chloride with counterions such as sulfate, phosphate, citrate, acetate, etc., which are more capable of accepting hydrogen bonds. Mason P E et al. (2005) J Phys Chem B 109:24185-24196.

The results shown in FIG. 7 reveal that a generation 0 PAMAM dendrimer with a surface modified to guanidinium dihydrogen phosphate ($H_2PO_4$) has an ability to slow the rate of aCgn aggregation far beyond that of ArgHCl. To elaborate, with no cosolute present, half of the original amount of protein was lost within only 30 minutes. When in the presence of a high concentration of ArgHCl (0.67 M), the half-life was extended to about 2.5 hours, which is similar to other commonly used excipients. However, when in the presence of the $H_2PO_4$ form of the surface modified dendrimer at a concentration of 0.2 M, the half-life was extended to about 25 hours, which is a full order of magnitude longer than the solution containing ArgHCl. This superior aggregation suppression is observed at all concentrations for that salt form, as shown in FIG. 8. In that figure, the relative rate constant for aCgn monomer loss is depicted, which is the observed rate constant when a cosolute is added to the solution relative to the rate of monomer loss in a buffer only solution. The figure also reveals that aggregation suppression improved with increasing size of the dendrimer, as indicated by the monotonic improvement in aggregation suppression with each dendrimer generation.

Improved aggregation suppression was also observed when the counterion was exchanged to other hydrogen bond accepting anions. When exchanged to acetate, aggregation suppression was only improved slightly, which was expected given that acetate cannot form as many hydrogen bonds with Gdm as compared to other ions. Schneider C P et al. (2011) J Phys Chem B 115:7447-7458. When chloride was exchanged with sulfate, however, the resulting compound showed nearly identical ability for inhibiting aggregation as the $H_2PO_4$ salt form. The sharp decline in the rate of aCgn aggregation prompted us to study dendrimer-aCgn interactions, both experimentally and computationally, to give greater mechanistic insight into the observed behavior. However, we first expanded the aggregation study to determine if the observations are observed for other proteins.

Concanavalin A (Con A) was used as another model protein for the aggregation study, which demonstrated that the shelf-life of this protein at pH 6.5 and 37° C. was extended by a factor greater than 15 when in the presence of the generation 1 dendrimer with a guanidinium sulfate surface (see Table 1), which is over 10 times longer than when in the presence of commonly used additives such as glycerol or sucrose.

TABLE 1

Protein solution shelf-life extension at accelerated conditions resulting from aggregation suppression induced by surface-modified PAMAM dendrimers and other commonly used additives formulated at isotonic concentrations.

| Additive | Gen. | Surface | Conc. mM | aCgn $t_{95}/t_{95,0}$ | Con A $t_{95}/t_{95,0}$ |
|---|---|---|---|---|---|
| Sucrose | — | — | 280 | 1.9 | 1.5 |
| Glycerol | — | — | 280 | — | 1.3 |
| Na$_2$SO$_4$ | — | — | 140 | 3.1 | 1.1 |
| ArgHCl | — | — | 170 | 3.3 | 0.4 |
| Dend. | 0 | Gdm(SO$_4$)$_{1/2}$ | 140 | 26.9 | 5.9 |
| Dend. | 0 | Gdm(H$_2$PO$_4$) | 80 | 18.9 | 1.6 |
| Dend. | 1 | Gdm(SO$_4$)$_{1/2}$ | 70 | — | 16.7 |
| Dend. | 1 | Gdm(H$_2$PO$_4$) | 42 | 16.3 | — |

The aCgn solution was formulated in a 20 mM sodium citrate pH 5 buffer and was incubated at 52.5° C. The Con A solution was formulated in a 40 mM sodium phosphate pH 6.5 buffer and was incubated at 37° C.

Table 1 depicts the factor by which the shelf-life of aCgn and Con A is extended when they are formulated with the modified dendrimers. This Shelf-Life Extension Factor was determined by comparing the length of time, $t_{95}$, for a 5% loss of protein when in the presence of the compounds to the original length of time, $t_{95,0}$ for a 5% loss. For comparison purposes, isotonic concentrations (as determined by VPO) of the compounds were used and Shelf-Life Extension Factor values for commonly used excipients at isotonic concentrations are shown as well. Shelf-life values of aCgn were determined at 52.5° C. and at 37° C. for Con A.

It is clear from these results that when utilized at a practical maximum concentration, the surface modified dendrimers, in the form of either a dihydrogen phosphate or sulfate salt, significantly improve the shelf life of these two proteins, either at high or moderate temperatures. For aCgn, the shelf life is extended by a factor between 16 and 27 when formulated with these dendrimers, which is 5 to 8 times longer than when in the presence of other aggregation suppressing additives, such as arginine HCl, sucrose, or sodium sulfate.

The results for Con A are more significant and show a much clearer relationship with the size of the dendrimers. At 37° C. and pH 6.5, Con A aggregates quite rapidly. Commonly used additives can extend the shelf life, at most, by factor of only 1.5. The sulfate form of the generation 0 modified dendrimer quadrupled this to a factor of 5.9, and the sulfate form of the generation 1 modified dendrimer extended the shelf life even further, by a factor of 16.7. The phosphate form only showed a minimal improvement in the shelf life, likely due to Con A being very sensitive to ionic strength at pH 6.5 because arginine HCl, sodium chloride, and sodium phosphate all promote Con A aggregation. The sulfate form of the dendrimers has fewer ions per mole than the phosphate form and therefore, the detrimental effect imparted on proteins that are sensitive to ionic strength is lessened when this form of the dendrimer is used.

It should be noted that these results do not extend completely to the original, unmodified dendrimer structure, which has an ammonium surface. The chloride form of the unmodified dendrimer is more destabilizing and the phosphate form is less effective at suppressing aggregation (see FIG. 8). This indicates that a Gdm surface is effective to produce the potent aggregation suppressing results through both protein-additive and ion-ion interactions.

Example 3

Conformational Stability

The thermostability of aCgn at 1 mg/mL in the presence of the modified dendrimers was assessed by determining the denaturation midpoint temperature ($T_m$) from DSC scans, which is a qualitative indicator of how the conformational stability of the protein is perturbed. Ghosh K et al. (2009) Proc Natl Acad Sci USA 106:10649-10654.

TABLE 2

Summary of key data for each guanidinium-modified PAMAM dendrimer salt, demonstrating their physical properties and their interaction with aCgn.

| Surface | MW g/mol | $\underline{V}_o$ L/mol | $\Gamma_{23}/[3]$ mol/mol | $dT_m/d[3]$ K * L/mol | Number of Hydrogen Bonds | | | | | |
|---|---|---|---|---|---|---|---|---|---|---|
| | | | | | D-D | D-A | D-A-D | P-D | P-A | P-A-D |
| GdmCl | 903.6 | 0.5217 | −8.1 ± 3.6 | −13.9 | 1 | 21 | 1 | 22 | 5 | 0 |
| Gdm(SO$_4$)$_{1/2}$ | 979.1 | 0.5665 | −17.0 ± 4.4 | 15.2 | 1 | 146 | 124 | 13 | 13 | 35 |
| Gdm(H$_2$PO$_4$) | 1272.8 | 0.7254 | −15.8 ± 5.0 | 37.4 | 5 | 150 | 73 | 14 | 18 | 32 |

MW—molecular weight,
$\underline{V}_o$—partial molar volume at infinite dilution,
[3]—molar concentration of the additive,
D—Dendrimer,
A—Anion, and
P—Protein.
Partial molar volume was determined from density measurements of gravimetrically prepared dendrimer only solutions.
Preferential interactions ($\Gamma_{23}$) with aCgn were determined by VPO, aCgn denaturation midpoint temperature ($T_m$) increments were determined by DSC, and the number of hydrogen bonds between different species was determined from MD simulations.
aCgn solutions for the $\Gamma_{23}$ (50 mg/mL) and $T_m$ (1 mg/mL) data contained 20 mM sodium citrate pH 5 buffer and a maximum dendrimer concentration of 0.2 mol/L.

As shown in Table 2, the sulfate and H$_2$PO$_4$ salt forms of the surfaced modified generation 0 dendrimers increased $T_m$ at a rate of 15.2 and 37.4° C.*M$^{-1}$, respectively, for concentrations less than 0.2 mol/L, while the chloride salt form decreased $T_m$ at a rate of 13.9° C.*M$^{-1}$. One can speculate that this indicates that the sulfate and H$_2$PO$_4$ salt forms shift the protein folding equilibrium toward the native structure while the chloride salt form promotes unfolding. However, given that the unfolding of aCgn is irreversible, it could also indicate that the sulfate and H$_2$PO$_4$ salt forms reduce the rate at which aCgn aggregates during the DSC scan. The apparent thermodynamic stabilization by these forms is quite significant when compared to other conformational stabilizers (e.g., sucrose) (Schneider C P et al. (2011) J Phys Chem B 115: 7447-7458) given that the results likely represent a combination of conformational stabilization and association suppression. The rate at which the chloride salt form lowers the melting temperature of aCgn is double that for ordinary GdmCl (Schneider C P et al. (2011) J Phys Chem B 115: 7447-7458) and given that this dendrimer salt form inhibits aggregation at low concentrations, this shows that this surface-modified dendrimer is a powerful denaturant.

Example 4

Ion-Ion Interactions

Molecular dynamics (MD) simulations were conducted on aqueous solutions of the modified generation 0 dendrimers to quantify how ion-ion interactions may be influencing the behavior of the additives. These simulations were performed using NAMD 2.7 (Phillips J C et al. (2005) J Comput Chem 26:1781-1802), with CHARMM27 (Brooks B R et al. (1983) J Comput Chem 4:187-217) force fields and the TIP3P (Jorgensen W L et al. (1983) Chem Phys 79:926-935) water model. The force field parameters for the counterions were taken from the literature (Cannon W R et al. (1994) J Phys Chem 98:6225-6230) and the force field parameters for the surface modified generation 0 dendrimer were developed using the CHARMM force field development procedure (MacKerell A D (2001) Atomistic Models and Force Fields. In: Becker O, MacKerell A D, Roux B, Watanabe M, editors. Computation Biochemistry and Biophysics. New York: Marcel Dekker Inc. pp. 7-38).

Figure 9:
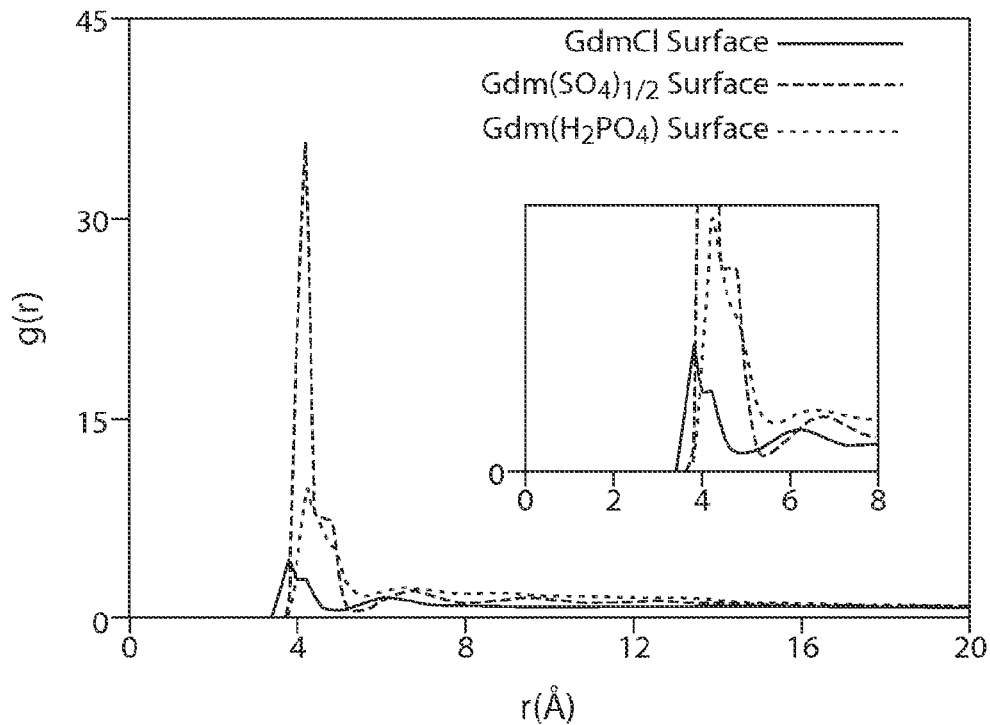
FIG. 9 is a graph depicting radial distribution functions (RDF's) between dendrimer and counterions. The distance between the centers of mass of the dendrimers is used for calculation of the RDF's. For the counterions, the sulfur atom in sulfate, phosphorus atom in $H_2PO_4$ are utilized.
Figure 10:
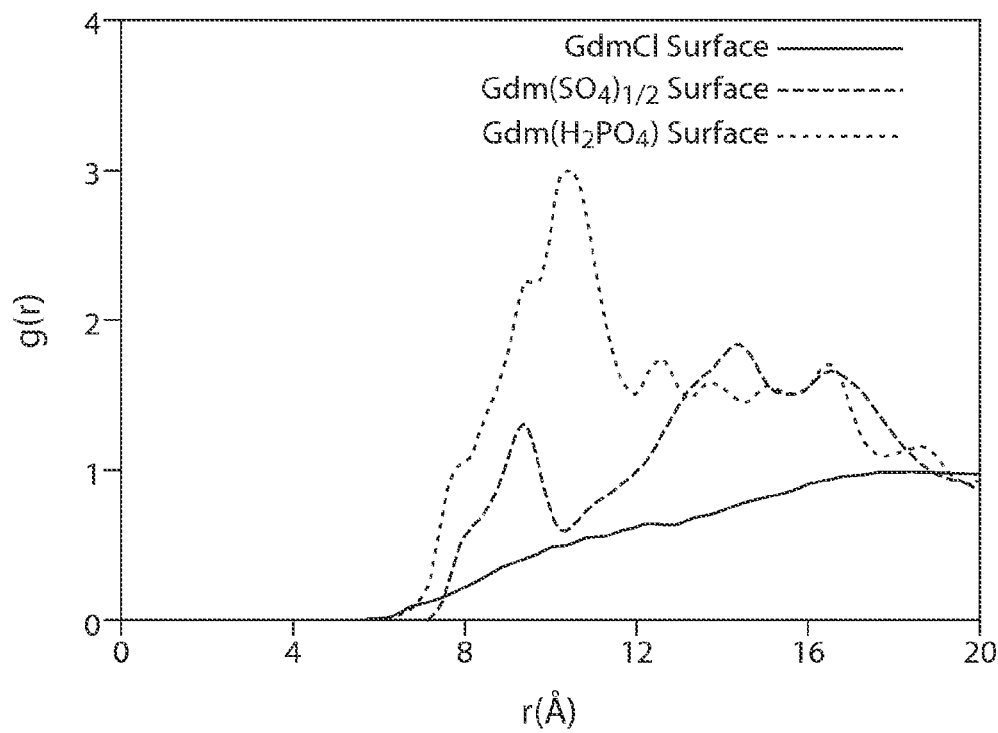
FIG. 10 is a graph depicting RDF's between dendrimer molecules in different dendrimer salt solutions.

In FIG. 9, the Radial Distribution Functions (RDF) between the dendrimer and the counterions show that the sulfate and H$_2$PO$_4$ ions interact strongly with the dendrimer molecules, as shown by the height of the peaks relative to chloride. In FIG. 10, the RDF's between dendrimer molecules indicate that, in the presence of chloride ions, dendrimer molecules do not interact with each other, however, the presence of sulfate and H$_2$PO$_4$ ions tends to bring dendrimer molecules together. This is further supported by MD snapshots of the simulation box, which show significant ion pairing in the sulfate and H$_2$PO$_4$ salt solutions while solutes in the chloride solution are randomly distributed. These results indicate that the Gdm group on the dendrimers can form charge-assisted hydrogen bonds with the sulfate and H$_2$PO$_4$ ions. The sulfate ion, which has a −2 charge on four oxygens, forms a much stronger hydrogen bond as compared to the H$_2$PO$_4$, which has −1 charge.

These results also show that counterions can act as a bridge between dendrimer molecules due to attractive guanidinium-anion interactions, leading to the formation of large clusters in solution. To verify and quantify this observation, the number of hydrogen bonds formed between different ion-pairs in aqueous modified dendrimer salt solutions was calculated from the simulation results (see Table 2). Sulfate and H$_2$PO$_4$ ions, due to the presence of multiple hydrogen bond donors and acceptors, indeed act as a bridge joining dendrimer molecules together. The number of hydrogen bonds for both salt types (~150) is nearly an order of magnitude more than that for the chloride form (~20), leading to numerous bridged interactions (73 to 124), which is almost nonexistent for the chloride form. These guanidinium-anion and bridged interactions have a direct impact on the number of dendrimer-protein interactions, reducing the number by nearly half when compared to the chloride form.

The extent of clustering in these solutions can also be quantified in terms of the loss of the solvent-accessible area (SAA) of dendrimer molecules, as shown in Table 3. The loss of SAA due to clustering is greatest for H$_2$PO$_4$ (~60%), followed by sulfate (~40%) and chloride (20%). In the case of chloride, the loss of SAA is mainly due to the presence of counterions near the dendrimer. For sulfate and H$_2$PO$_4$, the dominant component to the loss of SAA is due to the overlap of dendrimer molecules. The number of H$_2$PO$_4$ ions is twice the number of sulfate ions per dendrimer molecule, which contributes to the higher loss of SAA as compared to sulfate.

TABLE 3

Loss of solvent-accessible surface area (SAA) of modified generation 0 PAMAM dendrimers due to clustering in aqueous solutions.

| Surface | SAA (Å$^2$) | ΔSAA (Å$^2$) | ΔSAA (Å$^2$) dendrimer overlap | ΔSAA (Å$^2$) counter-ion overlap |
|---|---|---|---|---|
| GdmCl | 993 | 267 | 107 | 160 |
| Gdm(SO$_4$)$_{1/2}$ | 760 | 500 | 342 | 158 |
| Gdm(H$_2$PO$_4$) | 533 | 727 | 435 | 292 |

The SAA of a dendrimer molecule in water is 1260 Å$^2$.

Example 5

Preferential Interactions

To gain further insight into how the modified dendrimer salts inhibit protein-protein interactions, preferential interaction coefficient ($\Gamma_{23}$) values at various concentrations were determined, both experimentally via vapor pressure osmometry (VPO) measurements and computationally via MD simulations. The experimental results for the interaction between modified generation 0 PAMAM dendrimers and aCgn are expressed in Table 2, which summarizes the polynomial fit and uncertainty of the experimental data. Theoretical preferential interaction coefficient values were computed from the MD simulation using the procedure outlined in our previous work. Baynes B M and Trout B L (2003) J Phys Chem B 107:14058-14067; Shukla D et al. (2009) J Phys Chem B 113:12546-12554. Results are presented in Table 4.

TABLE 4

Preferential interaction coefficient values of α-Chymotrypsinogen A in aqueous modified generation 0 PAMAM dendrimer solutions.

| Surface | Conc. (mol/L) | $\Gamma_{exp}$ | $\Gamma_{MD}$ | $\Gamma_{MD}$ Dend. | $\Gamma_{MD}$ Anion |
|---|---|---|---|---|---|
| GdmCl | 0.18 | −1.5 | −0.2 | 1 | −7 |
| Gdm(SO$_4$)$_{1/2}$ | 0.18 | −3.1 | −2.7 | −3 | −7 |
| Gdm(H$_2$PO$_4$) | 0.17 | −2.9 | −2.3 | −3 | −10 |

Standard deviations on the preferential interaction coefficient values are ~1.

Figure 11:
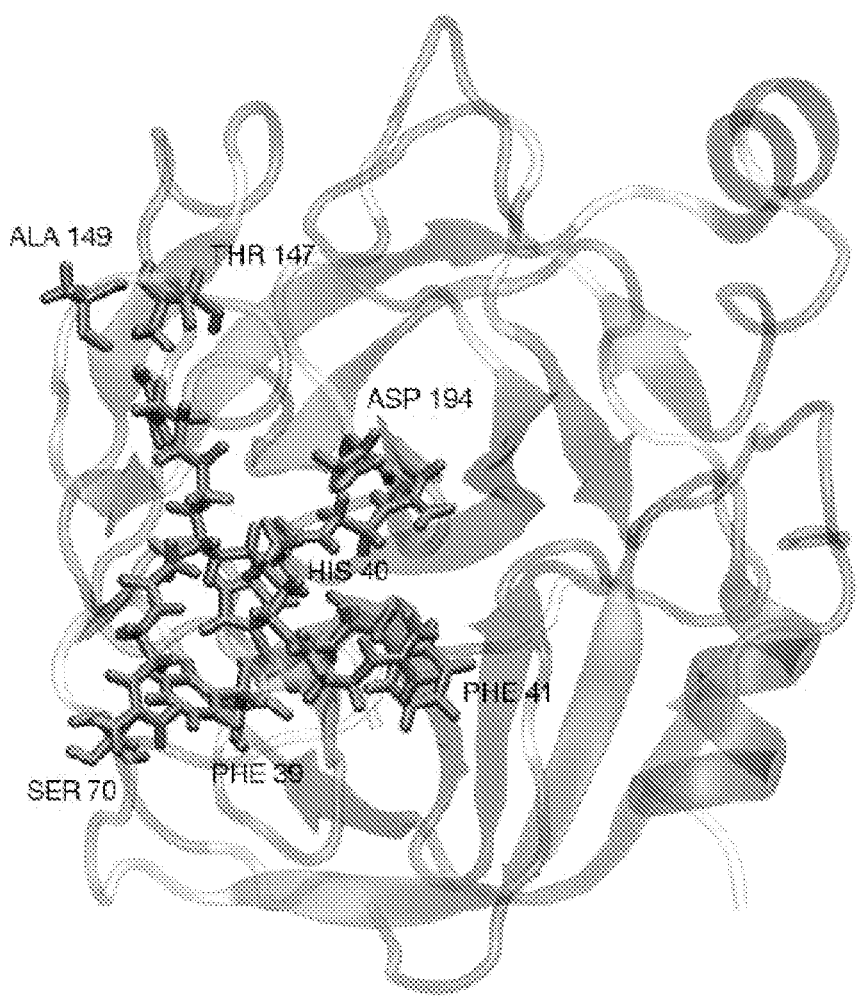
FIG. 11 is a computer-generated image depicting PAMAM dendrimer with guanidinium chloride surface interacting with multiple groups on the surface of aCgn. The guanidinium groups can hydrogen bond with negatively charged amino acids and the peptide backbone. They can also form cation-it interaction with aromatic amino acids. Side chains of amino acid residues Phe 39, H is 40, Phe 41, Ser 70, Ala 149, Thr 147, and Asp 194 of aCgn are highlighted and identified.

At a concentration of 0.18 mol/L, the theoretical preferential interaction coefficient for the chloride salt was found to be −0.2±1, which matches well with the experimental value of −1.5±0.7. The $\Gamma_{23}$ values for salts are a weighted average of the $\Gamma_{23}$ values for individual ions. $\Gamma_{23}$ for the dendrimer cation was found to have a positive value of 1, which shows that the local concentration of dendrimer molecules around the protein is higher than the bulk concentration. However, due to the negative preferential interaction value for the chloride ion (−7), the overall preferential interaction coefficient was found to be negative. The observed preferential binding of the dendrimer cation stems from the fact that the modified dendrimers can interact favorably with a variety of amino acids on the protein surface due to the presence of the Gdm group, which can form hydrogen bonds with negatively charged amino acids and the protein backbone and can also interact with aromatic amino acids via cation-π interactions. Furthermore, the dendrimer molecule can bind cooperatively with the protein surface due to multiple Gdm surface groups simultaneously interacting with the protein surface (see FIG. 11, which shows a snapshot of multiple, simultaneous interactions). However, switching the counterion to either sulfate or $H_2PO_4$ inhibits the occurrence of such multiple interactions.

$\Gamma_{23}$ values for the sulfate (−2.7) and $H_2PO_4$ (−2.3) salt forms matched well with their corresponding experimental values. The values of $\Gamma_{23}$ for the counterions are −10 for the $H_2PO_4$ ion and −7 for the sulfate ion, which is present in half the quantity as the phosphate and chloride ions. On the basis of the observed attractive interaction between the dendrimer and these counterions, it can be argued that sulfate and $H_2PO_4$ inhibit the dendrimer molecule from binding to the protein surface. In essence, the dendrimer molecules are pulled away from the surface to interact with bulk solution components. This is verified by the individual $F_{23}$ values for the dendrimer molecule (−3 for both salt types). These results are similar to the results of our recent work on the interaction of arginine with proteins, where the carboxylate group and various counterions limited the interaction between a protein and the Gdm group in arginine. Shukla D and Trout B L (2010) J Phys Chem B 114:13426-13438; Shukla D and Trout B L (2011) J Phys Chem B 115:1243-1253; Schneider C P et al. (2011) J Phys Chem B 115:7447-7458. As mentioned before, the reduced number of hydrogen bonds between the protein and the dendrimer (see Table 2) further supports this behavior. The loss in the number of direct hydrogen bonds is compensated by the increase in the number of indirect hydrogen bonds formed between the protein and the dendrimer in which the counterion acts as a bridge.

Figure 12:
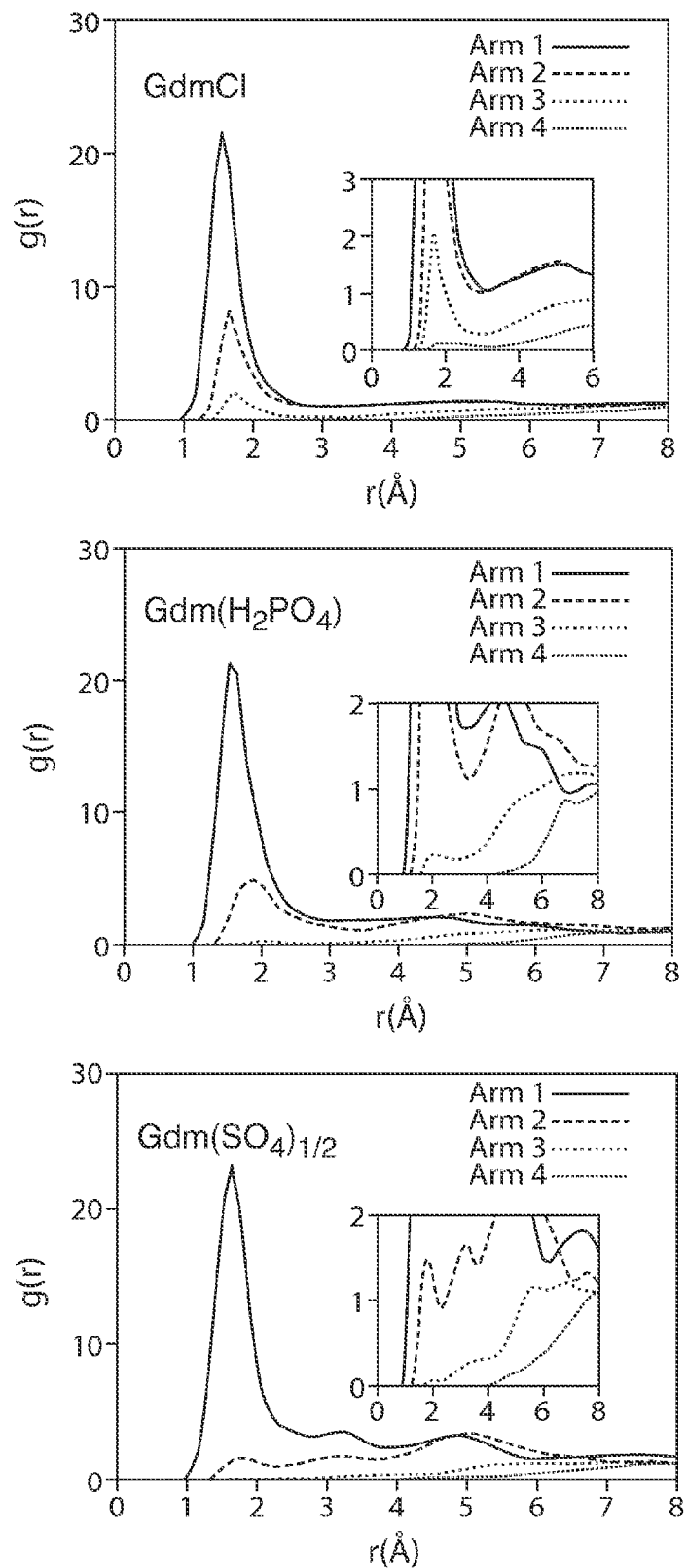
FIG. 12 is a series of three images depicting RDF's between α-chymotrypsinogen A and the surface guanidinium groups on the PAMAM dendrimer. The counterion is either chloride (upper image), $H_2PO_4$ (middle image), or sulfate (lower image). The arms of the dendrimer are labeled 1-4 depending on their distance from the protein surface, with 1 denoting the closest arm. The distance of the central carbon atom in the guanidinium group from the protein surface is used for the calculations.

RDF's between the four dendrimer arms and the protein surface (see FIG. 12) highlight the implications of the counterions interacting with the Gdm groups. The RDF for the closest arm remains almost the same for all dendrimer salts, but the RDF's for the remaining arms show a sharp decrease in peak height and increased distance from the surface of the protein for the sulfate and $H_2PO_4$ salt forms. This result further supports that for the dendrimer with a GdmCl surface, multiple arms simultaneously interact with the protein surface but for the sulfate and $H_2PO_4$ salts, only one arm can interact with the protein while the other arms face away from the surface and interact with the bulk solution. Furthermore, for the sulfate and $H_2PO_4$ salts, there are additional peaks further away from the surface for the closest dendrimer arm, which is the result of the anions acting as a bridge between the protein and the dendrimer. This interaction with the Gdm group is clearly impeding direct binding of the dendrimer to the protein surface.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A salt, comprising a plurality of anions; and a cation represented by formula I:

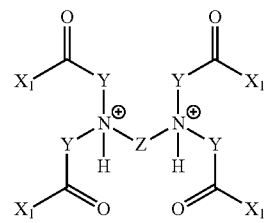

wherein, independently for each occurrence,
each anion is

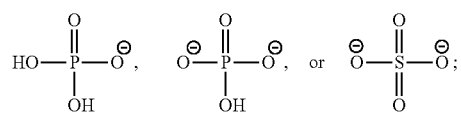

Z is —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
Y is —CH$_2$—, —CH$_2$CH$_2$—, —CH$_2$CH$_2$CH$_2$—, —CH$_2$CH$_2$CH$_2$CH$_2$—, or —CH$_2$CH$_2$CH$_2$CH$_2$CH$_2$—;
X$^1$ is

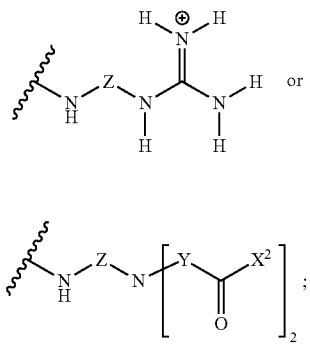

X$^2$ is

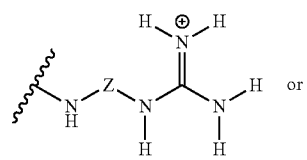

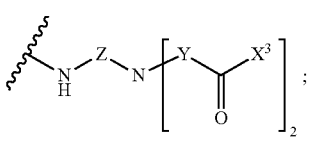

and
X³ is

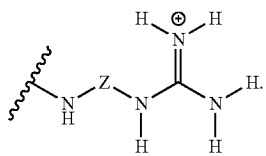

2. A salt, comprising a plurality of anions; and a cation represented by formula II:

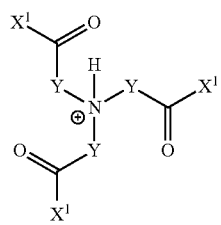

II wherein, independently for each occurrence, each anion is

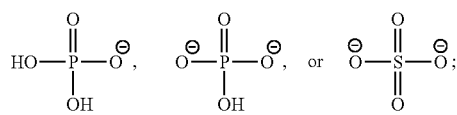

Z is —CH₂CH₂—, —CH₂CH₂CH₂—, —CH₂CH₂CH₂CH₂—, or —CH₂CH₂CH₂CH₂CH₂—;
Y is —CH₂—, —CH₂CH₂—, —CH₂CH₂CH₂—, —CH₂CH₂CH₂CH₂—, or —CH₂CH₂CH₂CH₂CH₂—;
X¹ is

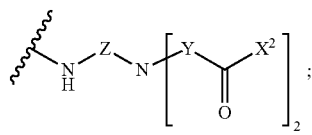

X² is

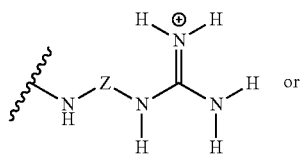

or

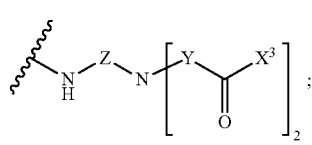

and
X³ is

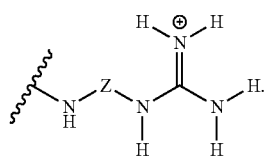

3. A salt, comprising a plurality of anions; and a cation represented by formula III:

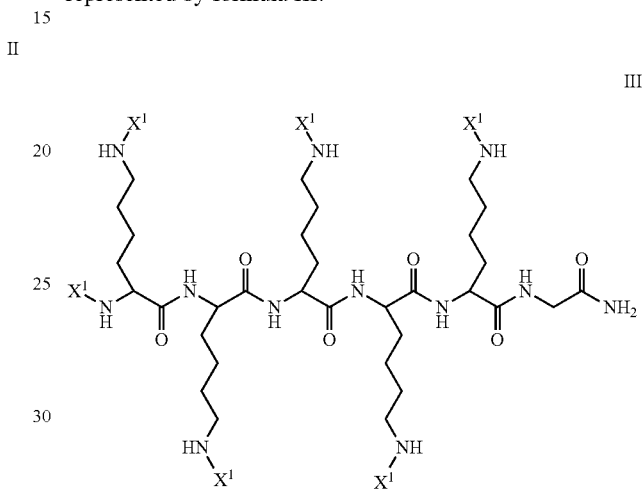

III wherein, independently for each occurrence, each anion is

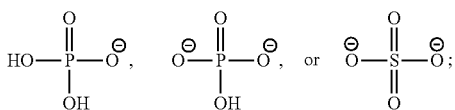

X¹ is

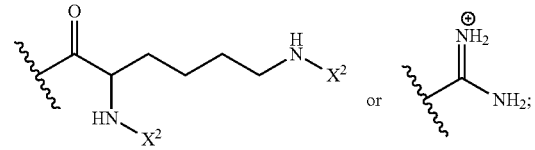

or

X² is

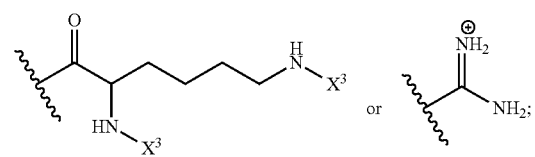

or $X^3$ is

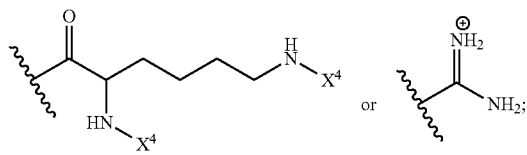 or 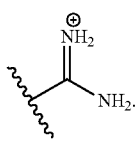 [SMILES: *C(N)=[NH2+]]

and
$X^4$ is

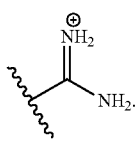 [SMILES: *C(N)=[NH2+]]

4. A salt, comprising a plurality of anions; and a cation represented by formula IV:

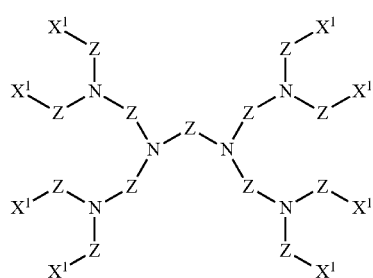

IV wherein, independently for each occurrence,
each anion is

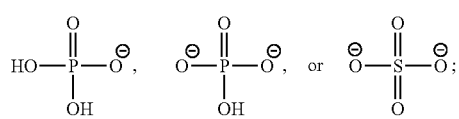

Z is —CH$_2$CH$_2$—, —CH$_2$CH$_2$CH$_2$—,
—CH$_2$CH$_2$CH$_2$CH$_2$—, or —CH$_2$CH$_2$CH$_2$CH$_2$CH$_2$—;
$X^1$ is

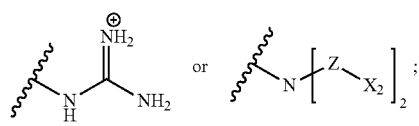

$X^2$ is

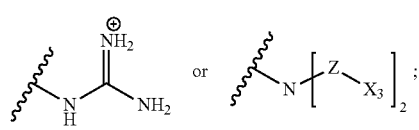

$X^3$ is

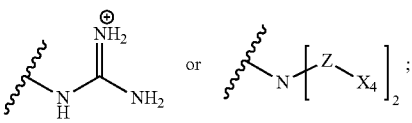

and
$X^4$ is

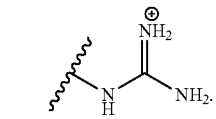

5. The salt of claim 1, wherein $X^1$ is

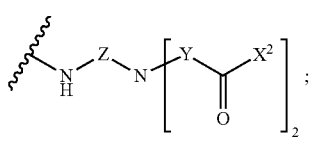

6. The salt of claim 1, wherein $X^1$ is

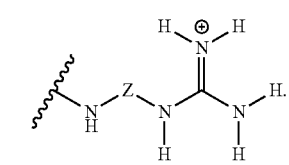

and $X^2$ is

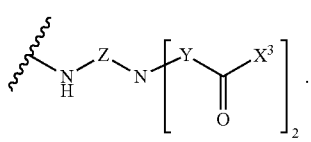

7. The salt of claim 1, wherein $X^1$ is

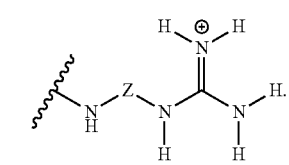

and $X^2$ is

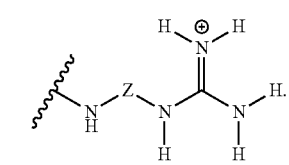

8. The salt of claim 1, wherein Z is —CH$_2$CH$_2$—.
9. The salt of claim 1, wherein Y is —CH$_2$CH$_2$—.
10. The salt of claim 1, wherein Y is —CH$_2$CH$_2$—; and Z is —CH$_2$CH$_2$—.

11. The salt of claim 1, wherein each anion is

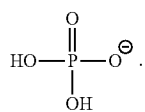

12. The salt of claim 1, wherein each anion is

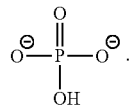

13. The salt of claim 1, wherein each anion is

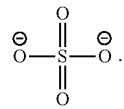

14. A composition, comprising a protein; and a salt of claim 1.

15. The composition of claim 14, wherein the protein is selected from the group consisting of antibodies and enzymes.

16. A method of increasing shelf life of an aqueous solution of a protein, comprising:
   combining an aqueous solution of a protein and an effective amount of a salt of claim 1.

17. The method of claim 16, wherein the protein is selected from the group consisting of antibodies and enzymes.

18. A method of decreasing the amount of protein aggregation in an aqueous solution of a protein, comprising:
   combining an aqueous solution of a protein and an effective amount of a salt of claim 1.

19. The method of claim 18, wherein the protein is selected from the group consisting of antibodies and enzymes.

* * * * *